(12) United States Patent
Ho et al.

(10) Patent No.: US 6,559,208 B2
(45) Date of Patent: *May 6, 2003

(54) METHOD OF MAKING WASHABLE, DRYABLE ELASTIC ARTICLES

(75) Inventors: Thoi H. Ho, Lake Jackson, TX (US); Edward N. Knickerbocker, Lake Jackson, TX (US); Rexford A. Maugans, Lake Jackson, TX (US)

(73) Assignee: Dow Global Technologies Inc., Midland, MI (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/321,370

(22) Filed: May 27, 1999

(65) Prior Publication Data

US 2002/0049269 A1 Apr. 25, 2002

Related U.S. Application Data

(60) Provisional application No. 60/087,536, filed on Jun. 1, 1998.

(51) Int. Cl.[7] .............................. C08K 5/55; C08K 5/33; B32B 27/08
(52) U.S. Cl. ..................... 524/186; 524/236; 524/251; 428/500; 428/515
(58) Field of Search ................................ 524/186, 236, 524/251; 428/500, 515

(56) References Cited

U.S. PATENT DOCUMENTS

| 5,272,236 A | 12/1993 | Lai et al. ................. 526/548.5 |
| 5,324,576 A | 6/1994 | Reed et al. .................. 428/224 |
| 5,451,450 A | 9/1995 | Erderly et al. ............... 428/220 |
| 5,472,775 A | 12/1995 | Obijeski et al. ............. 428/220 |

FOREIGN PATENT DOCUMENTS

| EP | 0 346 862 A2 | 12/1989 | ......... C08F/255/08 |
| WO | 94/25648 | 11/1994 | ............. D01F/6/30 |
| WO | 96/31568 | 10/1996 | ............. C08L/69/00 |
| WO | 97/12919 | 4/1997 | ............. C08F/8/00 |
| WO | 98/20065 | 5/1998 | ......... C08K/5/3435 |
| WO | 98/26001 | 6/1998 | ........... C08L/51/06 |

OTHER PUBLICATIONS

International Search Report dated Sep. 2, 1999 issued by the EPO acting as the International Searching Autority in PCT/US99/11745.

*Primary Examiner*—Peter D. Mulcahy
(74) *Attorney, Agent, or Firm*—Whyte Hirschboeck Dudek SC

(57) ABSTRACT

The present invention relates to a method of making improved polyolefinic elastic articles from cured, irradiated or crosslinked amorphous ethylene interpolymers. In particular, the invention relates to a method of making a shaped article (e.g. film or fiber) characterized by improved elevated temperature elasticity as well as washability and dryability. The inventive elastic article comprises a substantially cured, irradiated, or crosslinked (or curable, irradiated or crosslinkable) homogeneously branched ethylene interpolymer characterized as having a density less than 0.90 g/cm$^3$ and containing at least one nitrogen-containing stabilizer. The improved elastic article of the present invention is particularly suitable for use in applications where good elasticity must be maintained at elevated temperatures and after laundering such as, for example, elastic waist bands of undergarments and other clothing.

25 Claims, 3 Drawing Sheets

METHOD OF MAKING WASHABLE, DRYABLE ELASTIC ARTICLES

CROSS-REFERENCE TO RELATED APPLICATION

This application claims the priority benefit of US provisional application No. 60/0875536, filed Jun. 1, 1998, the disclosure of which is incorporated herein by reference, in its entirety.

FIELD OF THE INVENTION

The present invention relates to a method of making improved polyolefinic elastic articles from cured, irradiated or crosslinked amorphous ethylene interpolymers. In particular, the invention relates to a method of making a shaped article (e.g. film or fiber) characterized by improved elevated temperature elasticity as well as washability and dry ability. The inventive elastic article comprises a substantially cured, irradiated, or crosslinked (or curable, irradiated or crosslinkable) homogeneously branched ethylene interpolymer characterized as having a density less than 0.90 $g/cm^3$ and containing at least one nitrogen-containing stabilizer. The improved elastic article of the present invention is particularly suitable for use in applications where good elasticity must be maintained at elevated temperatures and after laundering such as, for example, elastic waist bands of undergarments and other clothing.

BACKGROUND OF THE INVENTION

Materials with excellent stretchability and elasticity are needed to manufacture a variety of disposal and durable articles such as, for example, incontinence pads, disposable diapers, training pants, clothing, undergarments, sports apparel, automotive trim, weather-stripping, gaskets, and furniture upholstery. Stretchability and elasticity are performance attributes which can, for example, function to effectuate a closely conforming fit to the body of the wearer or to the frame of the item. While numerous materials are known to exhibit excellent stress-strain properties and elasticity at room temperatures, it is often desirable for elastic materials to provide a conforming or secure fit during repeated use, extensions and retractions at elevated temperatures such as at body temperatures or in automobile interiors during summer months. Maintaining tight tolerances throughout temperature cycles are also instances where elevated temperature elasticity is important. Further, where an elastics material is employed in clothing or garment items, the material must maintain its integrity and elastic performance after laundering.

Disposable elastic articles are typically elastic composite materials prepared from a combination of polymer film, fibers, sheets and/or absorbent materials as well as a combination of fabrication technologies. Whereas elastic fibers can be prepared by well known processes such as spun bonding, melt blowing, melt spinning and continuous filament wounding techniques, the film and sheet forming processes typically involve known extrusion and coextrusion techniques, e.g., blown film, cast film, profile extrusion, injection molding, extrusion coating, and extrusion sheeting.

Conversely, durable elastic articles are often molded or profile items such as, for example, automotive door and window trim, clothing waist band threads or strips, and building weather-stripping. Such durable articles can be made by well known molding, thermoforming and profile technologies.

A material is typically characterized as elastic when it is characterized as having a high percent elastic recovery (i.e., a low percent permanent set) after application of a biasing force. Ideally, elastic materials are characterized by a combination of three, temperature independent properties, i.e., a low percent permanent set, a low stress or load at strain, and a low percent stress or load relaxation. That is, there should be at low to elevated service temperatures (1) a low stress or load requirement to stretch the material, (2) no or low relaxing of the stress or unloading once the material is stretched, and (3) complete or high recovery to original dimensions after the stretching, biasing or straining is discontinued.

Lycra® is the trademark of Dupont Fibers for its elastic spandex fibers. The U.S. International Trade Commission defines spandex fiber as a manufactured fiber in which the fiber-forming substance is a long-chain synthetic polymer comprised of at least 85 percent segmented polyurethane. Lycra is known to exhibit nearly ideal, temperature independent elastic properties rendering it very suitable for use in garments, sports apparel and swimsuits. However, one significant shortcoming of Lycra is it typically exhibits fair to poor elevated temperature serviceability and washability. Similar to ordinary uncrosslinked polyolefin-based elastic materials, Lycra articles tend to lose their integrity and shape and elastic properties when subjected to elevated service temperatures such as during laundering and drying. Another major shortcoming of Lycra is its cost. That is, Lycra tends to be extremely cost prohibitive for a many of applications.

Elastic materials such as films, strips, coating, ribbons and sheet comprising at least one substantially linear ethylene polymer are disclosed in U.S. Pat. No. 5,472,775 to Obijeski et al., the disclosure of which is incorporated herein by reference. However, U.S. Pat. No. 5,472,775 does not disclose the performance of these materials at elevated temperatures (i.e., at temperatures above room temperature), nor their performance after laundering.

WO 94/25647, the disclosure of which is incorporated herein by reference, discloses elastic fibers and fabrics made from homogeneously branched substantially linear ethylene polymers. The fibers are said to posses at least 50 percent recovery (i.e., less than or equal 50 percent permanent set) at 100 percent strain. However, there is no disclosure in WO 94/25647 regarding the elasticity of these fibers at elevated temperatures or the effects of laundering on these fibers.

WO 95/29197, the disclosure of which is incorporated herein by reference, discloses curable, silane-grafted substantially ethylene polymers which are useful in wire and cable coatings, weather-stripping, and fibers. In the Examples, inventive samples include fibers comprising silane-grafted substantially ethylene polymers having densities of 0.868 $g/cm^3$ and 0.870 $g/cm^3$. The inventive examples are shown to exhibit improved elastic recovery at elevated temperatures. However, there is no disclosure in WO 95/29197 regarding the percent stress or load relaxation performance at elevated temperatures for these silane-crosslinked fibers, nor is there any disclosure as to washability.

U.S. Pat. No. 5,324,576, the disclosure of which is incorporated herein by reference, discloses an elastic nonwoven web of microfibers of radiation crosslinked ethylene/alpha olefin copolymers, preferably having a density less than 0.9 $g/cm^3$. In the examples set forth in U.S. Pat. No. 5,324,576, ethylene polymers having polymer densities greater than or equal to 0.871 $g/cm^3$ are subjected to electron beam radiation. However, there is no disclosure regarding the elastic performance of these radiated polymers at elevated temperatures, nor is there any disclosure regarding their resistance to washing and drying.

U.S. Pat. No. 5,525,257 to Kurtz et al., the disclosure of which is incorporated herein by reference, discloses that low levels of irradiation of less than 2 megarads of Ziegler catalyzed linear low density ethylene polymer results in improved stretchability and bubble stability without measurable gelation. However, '257 provides no disclosure respecting the elasticity and/or washability at elevated temperatures.

U.S. Pat. No. 4,957,790 to Warren, the disclosure of which is incorporated herein by reference, discloses the use of pro-rad compounds and irradiation to prepare heat-shrinkable linear low density polyethylene films having an increased orientation rate during fabrication. In the examples provided therein, Warren employs Ziegler catalyzed ethylene polymers having densities greater than or equal to 0.905 g/cm$^3$.

Various compounds are disclosed in the art and/or sold commercially as high temperature stabilizers and antioxidants. However, the criteria employed to distinguish these compounds as stabilizers and antioxidants typically relates to their ability to resistance yellowing, crosslinking and/or the ill-effects of irradiation (e.g., gamma irradiation for purposes of sterilization).

In other instances, different types of stabilizers are equated to one another or are said to perform comparably. For example, it is known that hindered phenolic stabilizers (e.g., Irganox® 1010 supplied by Ciba-Geigy) can be as effective as hindered amine stabilizers (e.g., Chimassorb® 944 supplied by Ciba-Geigy), and vice versa. In a product brochure entitled, "Chimassorb 944FL: Hindered Amine Light Stabilizer Use and Handling", printed 1996, Ciba-Geigy states Chimassorb 9944 "gives long-term heat stability to polyolefins by a radical trapping mechanism similar to that of hindered phenols."

Further, there is some belief that there is no universally effective stabilizer for polymers as the definition for stability inevitably varies with each application. In particular, there is no effective stabilizer for washable, high temperature serviceable polyolefinic elastic materials.

In general, stabilizers are known to inhibit crosslinking. In regard to crosslinking generally, there are several disclosures relating to radiation resistant (e.g., gamma and electron beam) polymer compositions comprising amine stabilizers. Such disclosures typically teach relatively high levels of amine stabilizer (for example, greater than or equal to 0.34 weight percent) are required where inhibition of crosslinking, discoloration and other undesirable irradiation effects is desired. Another examples include stabilized disposal nonwoven fabrics (see, e.g., U.S. Pat. No. 5,200,443, the disclosure of which is incorporated herein by reference) and stabilized molding materials (e.g. syringes). Gamma sterilization resistant fibers, including amine coatings and the use of hybrid phenolic/amine stabilizers are also known. See, e.g., U.S. Pat. No. 5,122,593 to Jennings et al., the disclosure of which is incorporated herein by reference.

Stabilized polyethylene compositions with improved resistance to oxidation and improved radiation efficiency are also known. M. Iring et al. in "The Effect of the Processing Steps on the Oxidative Stability of Polyethylene Tubing Crosslinked by Irradiation", *Die Angew. Makromol. Chemie*, Vol. 247, pp. 225–238 (1997), the disclosure of which is incorporated herein by reference, teach that amine stabilizers are more effective towards inhibiting electron-beam irradiation effects (i.e., provide better resistance against oxidation) than hindered phenols.

WO 92/19993 and U.S. Pat. No. 5,283,101, the disclosures of which are incorporated herein by reference, discloses launderable retroreflective appliqués comprised of a multicomponent binder composition consisting of an electron-beam curable elastomer, crosslinker(s), and coupling agent(s) and optional colorants, stabilizers, flame retardants and flow modifiers. The allegedly inventive appliqués are said to be capable of withstanding ordinary household washing conditions as well as more stringent industrial washings without loss of retroreflectiveness. Illustrative examples of electron-beam curable elastomers of the binder are said to be "chlorosulfonated polyethylenes, ethylene copolymers comprising at least about 70 weight percent of polyethylene such as ethylene/vinyl acetate, ethylene/acrylate, and ethylene/acrylic acid, and poly(ethylene-co-propylene-co-diene) ("EPDM") polymers." Optional stabilizers are described to be "thermal stabilizers and antioxidants such as hindered phenols and light stabilizers such as hindered amines or ultraviolet stabilizers". Although there is an equating of the suitability or effectiveness of hindered phenols to hindered amines in the descriptions of WO 92/19993 and U.S. Pat. No. 5,283,101, no stabilizer of any kind is exemplified in the provided examples. Further, although the appliqué can employ polymers that are described as "highly flexible" before and after electron-beam curing, neither the selected polymers nor the appliqué itself are described as "elastic". That is, a material can be highly flexible yet nonelastic as the terms "nonelastic" and "elastic" are defined herein below. However, the reverse is not true; elastic materials are characterized as having a high degree of flexibility (i.e., Young's Modulus of less than 10,000 psi (68.9 MPa) where lower modulus means more flexibility).

Although there is an abundance of art related to elastic ethylene polymer articles, including articles comprising curable, radiated and/or crosslinked ethylene polymers, and an abundance of art related to stabilized compositions and articles, there is no known disclosure of a polyolefinic elastic material with effective additive stabilization wherein the stabilization does not inhibit the desirable effects of irradiation and/or crosslinking (designed to impart elevated temperature elasticity and an increased melting point) and yet does inhibit the loss of elastic integrity (i.e. scission) when the material is subjected to a detergent washing and drying at elevated temperatures. Further, in another product brochure entitled, "Stabilization of Adhesives and Their Components", pp. 8–9 (1994), Ciba-Geigy, a premier stabilizer supplier, states that scission occurring in elastomeric materials (e.g. styrene-isoprene-styrene block copolymers) at elevated temperatures above 70° C. is not readily controlled by the use of antioxidants.

As such, there is a present need for cost-effective, stable elastic articles having good elasticity at elevated temperatures as well as good washability and dryability. That is, there is a need for elastic articles which retain their shapes under strain at elevated temperature (for example, greater than or equal to 125° C.). There is also a need for a method of making elastic articles having good elasticity at elevated temperatures and good wash/dry stability. We have discovered that these and other objects can be completely met by the invention herein described.

SUMMARY OF THE INVENTION

We have discovered that elastic articles comprising curable, irradiated and/or crosslinkable ethylene interpolymers characterized by a polymer density of less than 0.90 g/cm$^3$ at 23° C. and at least one nitrogen-containing stabilizer exhibit excellent elasticity at room temperature and at elevated temperatures as well as excellent wash and dry stability. According to the broad aspect of the invention, there is provided a method of making a shaped curable, irradiated or crosslinkable article comprising at least one homogeneously branched ethylene interpolymer, which comprises ethylene interpolymerized with at least one other monomer and characterized as having (before being shaped, grafted, cured, irradiated, or crosslinked) a polymer density of less than 0.90 g/cm$^3$ at 23° C., and at least one nitrogen-containing stabilizer.

Another aspect of the invention is a method of making a shaped and cured, irradiated or crosslinked article comprising at least one homogeneously branched ethylene interpolymer, which comprises ethylene interpolymerized with at least one other monomer and characterized as having (before being shaped, grafted, cured, irradiated, or crosslinked) a polymer density of less than 0.90 g/cm$^3$ at 23° C., and at least one nitrogen-containing stabilizer.

A third aspect of the invention is a method of making an elastic article comprising the steps of:

(a) providing at least one homogeneously branched ethylene interpolymer having a density of less than 0.90 g/cm$^3$ at 23° C. having at least 0.1 weight percent of at least one nitrogen-containing stabilizer therein, (b) fabricating or shaping the article from the interpolymer, and (c) after the fabrication or shaping, subjecting the article to heat and/or ionizing radiation, wherein the article is characterized as having:

(i) a percent permanent set of less than or equal 25 at 23° C. and 200 percent strain when measured at a 2 mil (102 mm) thickness using an Instron tensiometer after being shaped and cured, irradiated or crosslinked, (ii) a percent stress relaxation of less than or equal 25 at 23° C. and 200 percent strain when measured at a 2 mil thickness using a Instron tensiometer after being shaped and cured, irradiated or crosslinked, and (iii) a percent stress relaxation of less than or equal 55 at 38° C. and 200 percent strain when measured at a 2 mil thickness using an Instron tensiometer after.

A fourth aspect of the invention is a method of making an elastic article wherein the steps further comprises incorporating a pro-rad crosslink additive into the interpolymer.

A fifth aspect of the invention is a method of making a curable elastic article comprising the steps of:

(a) providing at least one homogeneously branched ethylene interpolymer characterized as having a density at 23° C. less than 0.90 g/cm$^3$ and comprising at least 0.1 weight percent of at least one nitrogen-containing stabilizer incorporated therein, (b) preparing a melt of the stabilized interpolymer of (a);

(c) mixing into the melt of (b) from about 0.5 to about 5 phr of a silane crosslinker (parts of silane crosslinker per hundred parts interpolymer) while the crosslinker is at an ambient temperature between 0 and 30° C.; and (d) subjecting the melt mixture of (c) to ionizing energy or contacting the melt mixture of (c) with at least one free radical initiator to graft at least about 50 weight percent, based on the total weight of the crosslinker and the interpolymer, of the silane crosslinker to the stabilized interpolymer.

Preferably, the article is fabricated or shaped using an extrusion technique (i.e., the method consists of melting the interpolymer) such as, for example, a fiber melt spinning, fiber melt blowing, film blowing, cast film, injection molding, or rotomolding technique, and is permitted to cool or is quenched to ambient temperature (i.e., permitted to substantially solidify) before the application or exposures to (additional) heat, ionizing radiation and/or moisture.

In a preferred embodiment of the invention, the at least one homogeneously branched ethylene interpolymer is a substantially linear ethylene interpolymer. In another preferred embodiment, the ionizing radiation is provided by electron beam irradiation. In a third preferred embodiment, the at least one nitrogen-containing stabilizer is a hydroquinoline, diphenylamine or substituted piperidine.

We discovered that there is a subset of ethylene polymers which provide completely unexpected elastic performance results when cured, radiated and/or crosslinked. In particular, we found for a broad range of polymer densities, curing, radiation and/or crosslinking can dramatically decrease percent permanent set performance (i.e., improve elasticity or elastic recovery) and have no substantial-effects on ambient percent stress or load relaxation performance. However, while tending to adversely affect (i.e., increase) or have no affect on percent stress or load relaxation at elevated temperatures for polymer having densities equal to or greater than 0.865 g/cm$^3$, surprisingly curing, radiation and crosslinking decreases (i.e., improves) the elevated temperature percent stress or load relaxation performance of ethylene interpolymer having a polymer density less than 0.865 g/cm$^3$ or a DSC crystallinity at 23° C. less than 8.5 weight percent. That is, curing, radiating and/or crosslinking is an effective means for providing elastic materials and articles characterized as having excellent elevated temperature stress relaxation characteristics.

Not only is the dramatically different response to irradiation or crosslinking surprisingly in itself, these results are surprising for another reasons as well. For example, these results are surprisingly and unexpected because at a density less than 0.90 g/cm$^3$, ethylene interpolymers are already substantially amorphous. That is, a cross-over or transition in elastic performance attributable to curing, radiation and/or crosslinking would ordinarily be expected to relate to the amorphosity of the polymer; however, according to hexane extraction data at 50° C., determined according to the Food and Drug Administration (FDA) test method set forth under 21 37 C.F.R. §§177.1520 (d)(3)(ii), ethylene polymers are substantially amorphous at a density of 0.89 g/cm$^3$ and below. Given such small differences in amorphosity or crystallinity, dramatic elasticity differences in response to irradiation or crosslinking simply would not ordinarily be expected.

As another surprise, we discovered that the incorporation of at least one nitrogen-containing stabilizer imparts excellent laundering characteristics to the elastic article. This discovery is surprising and unexpected because the stabilizer does not inhibit or interfere with effective curing, radiation effects, crosslinking or crosslinking effects (and as such permits substantial melting point increases, i.e., from less than 75° C. to greater than 125° C.), yet inhibits melting and flowing (i.e., scission) from occurring at substantially elevated temperatures (e.g., 133° C.) in a wash/extend dry testing.

The washing and drying performance results of the inventive article are also surprising for at least one other reason. That is, the effectiveness of the at least one nitrogen-containing stabilizer is unexpected because in ordinary stabilization tests (e.g., inhibition of yellowing) nitrogen-containing stabilizers perform comparable to phenolic stabilizers, yet phenolic stabilizers do not inhibit melting and flowing in wash/dry testing.

DETAILED DESCRIPTION OF THE INVENTION

Figure 1:
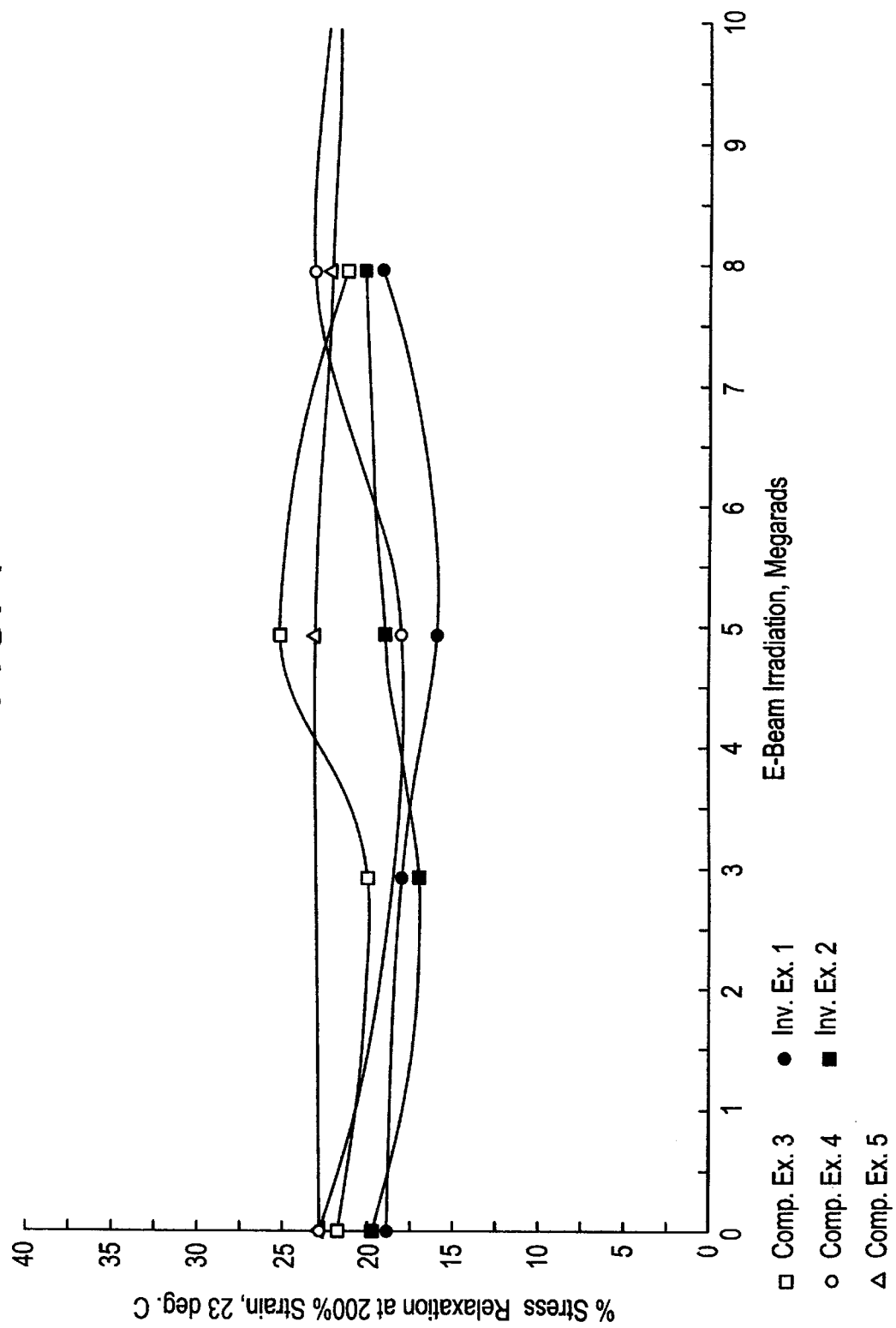
FIG. 1 is a plot of percent stress relaxation at 23° C. versus megarads of electron beam radiation for Inventive Examples 1 and 2 and comparative examples 3, 4 and 5.

The term "elastic" as used herein refers to a material having a permanent set of less than 60 percent, especially less than or equal to 25 percent (that is, especially greater than or equal to 87.5 percent recovery) at 200 percent strain (wherein 200 percent strain is, for example, stretching a 1 inch article to a final dimension of 3 inches). Elastic materials are more than simply highly flexible as in addition to having a Young's Modulus of less than 10,000 psi, they are defined a low percent permanent set at 200 percent strain. Elastic materials are also referred to in the art as "elastomers" and "elastomeric".

The term "nonelastic" as used herein means the material or article is not elastic as defined herein (i.e. the martial or article has a percent permanent set greater than 25).

Elastic materials and articles include, the cured, radiated and/or crosslinked ethylene interpolymer itself as well as, but are not limited, a fiber, film, strip, tape, ribbon, sheet, coating, and molding comprised of the cured, radiated and/or crosslinked ethylene interpolymer. Preferred elastic articles are fiber and film.

The term "radiated" or "irradiated" as used herein means the ethylene polymer, the shaped ethylene interpolymer or the article comprised of the ethylene polymer was subjected to at least 3 megarads (or the equivalent thereof) of ionizing energy whether or not there was a measurable decrease in percent xylene extractables (i.e., increase in insoluble gel). That is, substantial crosslinking may not result from the irradiation.

The terms "crosslinked" and "substantially crosslinked" as used herein mean the ethylene polymer, the shaped ethylene interpolymer or the article comprised of the ethylene polymer is characterized as having xylene extractables of less than 85 weight percent, preferably less than or equal to 75 weight percent, more preferably less than or equal to 70 weight percent, where xylene extractables are determined in accordance with ASTM D-2765.

The terms "cured" and "substantially cured" as used herein means the ethylene interpolymer, the shaped ethylene interpolymer or the article comprised of the ethylene interpolymer was subjected or exposed to a treatment which induced crosslinking. As used herein, the terms relate to ethylene interpolymers comprising a grafted silane.

The terms "curable" and "crosslinkable" as used herein mean the ethylene interpolymer, the shaped ethylene interpolymer or the article comprised of the ethylene interpolymer is not crosslinked and has not been subjected or exposed to treatment which induces crosslinking although the ethylene interpolymer, the shaped ethylene interpolymer or the article comprised of the ethylene interpolymer comprises additive(s) or functionality which will effectuate crosslinking upon subjection or exposure to such treatment.

The term "pro-rad additive" as used herein means a compound which is not activated during normal fabrication or processing of the homogeneously branched ethylene interpolymer, however can be activated by the application of temperatures (heat) substantial above normal fabrication or processing temperatures and/or by ionizing energy to effectuate some measurable gelation or preferably, substantial crosslinking.

The term "homofil" as used herein refers to fiber which has a single polymer region or domain and does not have any other distinct polymer regions (as do bicomponent fibers).

The term "meltblown" is used herein in the conventional sense to refer to fibers formed by extruding a molten thermoplastic polymer composition through a plurality of fine, usually circular, die capillaries as molten threads or filaments into converging high velocity gas streams (e.g. air) which function to attenuate the threads or filaments to reduced diameters. Thereafter, the filaments or threads are carried by the high velocity gas streams and deposited on a collecting surface to form a web of randomly dispersed meltblown fibers with average diameters generally smaller than 10 microns.

The term "spunbond" is used herein in the conventional sense to refer to fibers formed by extruding a molten thermoplastic polymer composition as filaments through a plurality of fine, usually circular, die capillaries of a spinneret with the diameter of the extruded filaments then being rapidly reduced and thereafter depositing the filaments onto a collecting surface to form a web of randomly dispersed spunbond fibers with average diameters generally between about 7 and about 30 microns.

The term "nonwoven" as used herein and in the conventional sense means a web or fabric having a structure of individual fibers or threads which are randomly interlaid, but not in an identifiable manner as is the case for a knitted fabric. The elastic fiber of the present invention can be employed to prepare nonwoven fabrics as well as composition structures comprises elastic nonwoven fabric in combination with nonelastic materials.

The term "conjugated" refers to fibers which have been formed from at least two polymers extruded from separate extruders but meltblown or spun together to form one fiber. Conjugated fibers are sometimes referred to in the art as multicomponent or bicomponent fibers. The polymers are usually different from each other although conjugated fibers may be monocomponent fibers. The polymers are arranged in substantially constantly positioned distinct zones across the cross-section of the conjugated fibers and extend continuously along the length of the conjugated fibers. The configuration of conjugated fibers can be, for example, a sheath/core arrangement (wherein one polymer is surrounded by another), a side by side arrangement, a pie arrangement or an "islands-in-the sea" arrangement. Conjugated fibers are described in U.S. Pat. No. 5,108,820 to Kaneko et al.; U.S. Pat. No. 5,336,552 to Strack et al.; and U.S. Pat. No. 5,382,400 to Pike et al., the disclosures of all of which are incorporated herein by reference. The elastic fiber of the present invention can be in a conjugated configuration, for example, as a core or sheath, or both.

The at least one homogeneously branched ethylene interpolymer to be irradiated, cured and/or crosslinked has a density at 23° C. less than 0.90 g/cm$^3$, preferably less than or equal to 0.865 g/cm³, more preferably in the range of about 0.865 g/cm³ to about 0.855 g/cm³, as measured in accordance with ASTM D792. At densities higher than 0.90 g/cm³, the interpolymer is not substantially amorphous or elastic, even at room temperature. Further, while at densities of equal to or less than 0.87 g/cm³, the benefits of effective stabilization can be realized, densities of equal to or less than 0.865 g/cm³ are preferred because the desired improvement in high temperature elastic performance (especially, a low percent stress or load relaxation) is obtained.

Preferably, the homogeneously branched ethylene interpolymer is characterized as having a DSC crystallinity of less than or equal to 8.3 weight percent, more preferably less than or equal to 8 weight percent and most preferably less than or equal 6 percent.

Preferably, the homogeneously branched ethylene interpolymer is characterized as having a melt index less than 10 g/10 minutes, as determined in accordance with ASTM D-1238, Condition 190° C./2.16 kilogram (kg).

The irradiated, cured and/or crosslinked article of the present invention is characterized as having a percent permanent set of less than 60 at 23° C., preferably less than or equal to 25 at 23° C., more preferably less than or equal to 20 and most preferably less than or equal to 15 at 23° C. and 38° C. and 200 percent strain when measured at a 2 mil thickness using an Instron tensiometer.

The irradiated, cured and/or crosslinked article of the present invention (and is characterized as having a percent stress relaxation of less than or equal 25 at 23° C. and 200 percent strain and less than or equal to 55, preferably less than or equal to 50, more preferably less than or equal to 30, most preferably less than or equal to 20 at 38° C. and 200 percent strain when measured at a 2 mil thickness using a Instron tensiometer.

Irradiation may be accomplished by the use of high energy, ionizing electrons, ultra violet rays, X-rays, gamma rays, alpha particles, protons, and beta particles and combination thereof. However, electron-beam irradiation is preferred. The irradiation is preferably carried out at a dosage up to 70 megarads, more preferably between about 3 megarads to about 35 megarads, most preferably between about 4 to about 30 megarads. Further, the irradiation can be carried out conveniently at room temperature, although higher and lower temperatures, for example 0° C. to about 60° C., may also be employed. Preferably, the irradiation is carried out after shaping or fabrication of the article. Also, in a preferred embodiment, the homogeneously branched ethylene interpolymer with a pro-rad additive incorporated therein is irradiated with electron beam radiation at about 8 to about 20 megarads.

The electron-beam irradiation source can be any suitable electron-beam generator. For example, suitable electron-bean irradiation equipment is available from Energy Services, Inc. Wilmington, Mass. with capabilities of at least 100 KeV and at least 5 Kw. The voltage can be adjusted to appropriate levels such as, for example, 100,000, 300,000, 1,000,000 or 2,000,000 or 3,000,000 or 6,000,000 or higher or lower. Many other apparati for irradiating polymeric materials are also known in the art.

The ethylene homogeneously branched interpolymer may be crosslinked or cured by first grafting a silane onto its polymer backbone and thereafter subjecting or exposing the silane grafted ethylene interpolymer to water or atmospheric moisture. Preferably, the silane grafted ethylene polymer is subjected or exposed to water or atmospheric moisture after a shaping or fabrication operation.

Suitable silanes for silane crosslinking of the ethylene interpolymer include those of the general formula

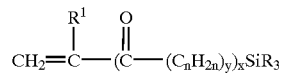

in which R' is a hydrogen atom or methyl group; x and y are 0 or 1 with the proviso that when x is 1, y is 1; n is an integer from 1 to 12 inclusive, preferably 1 to 4, and each R independently is a hydrolyzable organic group such as an alkoxy group having from 1 to 12 carbon atoms (e.g. methoxy, ethoxy, butoxy), aryloxy group (e.g. phenoxy), araloxy group (e.g. benzyloxy), aliphatic acyloxy group having from 1 to 12 carbon atoms (e.g. formyloxy, acetyloxy, propanoyloxy), amino or substituted amino groups (alkylamino, arylamino), or a lower alkyl group having 1 to 6 carbon atoms inclusive, with the proviso that not more than one of the three R groups is an alkyl.

Suitable silanes may be grafted to a suitable ethylene polymer by the use of a suitable quantity of organic peroxide, either before or during a shapingor fabrication operation. However, preferably, the silane is grafted onto the ethylene interpolymer before shaping or fabrication operations. In any case, the curing or crosslinking reaction takes place following the shaping or fabrication operation by reaction between the grafted silane groups and water. The water permeating into the bulk polymer from the atmosphere or from a water bath or "sauna". The phase of the process during which the crosslinks are created is commonly referred to as the "cure phase" and the process itself is commonly referred to as "curing".

Any silane that will effectively graft to and crosslink the ethylene interpolymer can be used in the present invention. Suitable silanes include unsaturated silanes that comprise an ethylenically unsaturated hydrocarbyl group, such as a vinyl, allyl, isopropenyl, butenyl, cyclohexenyl or γ-(meth) acryloxy allyl group, and a hydrolyzable group, such as, for example, a hydrocarbyloxy, hydrocarbonyloxy, or hydrocarbylamino group. Examples of hydrolyzable groups include methoxy, ethoxy, formyloxy, acetoxy, proprionyloxy, and alkyl or arylamino groups. Preferred silanes are the unsaturated alkoxy silanes which can be grafted onto the polymer. These silanes and their method of preparation are more fully described in U.S. Pat. No. 5,266,627 to Meverden, et al. Vinyl trimethoxy silane, vinyl triethoxy silane, γ-(meth) acryloxy propyl trimethoxy silane and mixtures of these silanes are the preferred silane crosslinkers for use in this invention. If a filler (e.g. calcium carbonate, talc, mica, silica (for example, SiO₂, clay, and aluminum trihydrate,) is present, then preferably the crosslinker includes vinyl triethoxy silane.

The amount of silane crosslinker used in the present invention can vary widely depending several factors such as the silane itself, processing conditions, grafting efficiency, organic peroxide selection, the ultimate application, and similar factors. However, typically at least 0.5, preferably at least 0.7, parts per hundred resin (phr) is used. Considerations of convenience and economy are usually the two principal limitations on the maximum amount of silane crosslinker used, and typically the maximum amount of silane crosslinker does not exceed 5, preferably it does not exceed 2, phr. As used in parts per hundred resin or phr, "resin" means the ethylene interpolymer.

The silane crosslinker is grafted to the ethylene interpolymer by any conventional method, typically in the presence of a free radical initiator e.g. peroxides and azo compounds, or by ionizing radiation, etc. A suitable grafting method is disclosed in WO 95/29197, the disclosure of which is incorporated herein by reference.

However, for efficient silane grafting, organic initiators are preferred, such as any one of the peroxide initiators, for example, dicumyl peroxide, di-tert-butyl peroxide, t-butyl perbenzoate, benzoyl peroxide, cumene hydroperoxide, t-butyl peroctoate, methyl ethyl ketone peroxide, 2,5-dimethyl-2,5-di(t-butyl peroxy)hexane, lauryl peroxide, and tert-butyl peracetate. A suitable azo compound is azobisisobutyl nitrite. The amount of initiator can vary, but it is typically present in an amount of at least 0.04, preferably at least 0.06, phr. Typically, the initiator does not exceed 0.15, preferably it does not exceed about 0.10, phr. The ratio of silane crosslinker to initiator also can vary widely, but the typical crosslinker:initiator ratio is between 10:1 to 30:1, preferably between 18:1 and 24:1.

While any conventional method can be used to graft the silane crosslinker to the substantially linear ethylene polymer, one preferred method is blending the two with the initiator in the first stage of a reactor extruder, such as a Buss kneader. The grafting conditions can vary, but the melt temperatures are typically between 160 and 260 C, preferably between 190 and 230 C, depending upon the residence time and the half life of the initiator.

Cure is can be promoted with a crosslinking catalyst, and any catalyst that will provide this function can be used. Suitable catalysts generally include organic bases, carboxylic acids, and organometallic compounds and combinations thereof including organic titanates and complexes or carboxylates of lead, cobalt, iron, nickel, zinc and tin. Representative catalyst include, for example, but is not limited to, dibutyltindilaurate, dioctyltinmaleate, dibutyltindiacetate, dibutyltindioctoate, stannous acetate, stannous octoate, lead naphthenate, zinc caprylate, and cobalt naphthenate. Tin carboxylate, especially dibutyltindilaurate and dioctyltinmaleate, are particularly effective for this invention. The catalyst (or mixture of catalysts) is present in a catalytic amount, typically between about 0.015 and about 0.035 phr.

Representative pro-rad additives include, but are not limited to, azo compounds, organic peroxides and polyfunctional vinyl or allyl compounds such as, for example, triallyl cyanurate, triallyl isocyanurate, pentaerthritol tetramethacrylate, glutaraldehyde, ethylene glycol dimethacrylate, diallyl maleate, dipropargyl maleate, dipropargyl monoallyl cyanurate, dicumyl peroxide, di-tert-butyl peroxide, t-butyl perbenzoate, benzoyl peroxide, cumene hydroperoxide, t-butyl peroctoate, methyl ethyl ketone peroxide, 2,5-dimethyl-2,5-di(t-butyl peroxy)hexane, lauryl peroxide, tert-butyl peracetate, azobisisobutyl nitrite and combination thereof. Preferred pro-rad additives for use in the present invention are compounds which have polyfunctional (i.e. at least two) moieties such as C=C, C=N or C=O.

At least one pro-rad additive can be introduced to the homogeneously branched ethylene interpolymer by any method known in the art. However, preferably the pro-rad additive(s) is introduced via a masterbatch concentrate comprising the same or different base resin as the ethylene interpolymer. Preferably, the pro-rad additive concentration for the masterbatch is relatively high e.g., about 25 weight percent (based on the total weight of the concentrate).

The at least one pro-rad additive is introduced to the homogeneously branched ethylene polymer in any effective amount. Preferably, the at least one pro-rad additive introduction amount is from about 0.001 to about 5 weight percent, more preferably from about 0.005 to about 2.5 weight percent and most preferably from about 0.015 to about 1 weight percent (based on the total weight of the ethylene interpolymer.

The term "polymer", as used herein, refers to a polymeric compound prepared by polymerizing monomers, whether of the same or a different type. As used herein, generic term "polymer" embraces the terms "homopolymer," "copolymer," "terpolymer" as well as "interpolymer."

The term "interpolymer", as used herein refers to polymers prepared by the polymerization of at least two different types of monomers. As used herein the generic term "interpolymer" includes the term "copolymers" (which is usually employed to refer to polymers prepared from two different monomers) as well as the term "terpolymers" (which is usually employed to refer to polymers prepared from three different types of monomers).

The term "homogeneously branched ethylene polymer" is used herein in the conventional sense to refer to an ethylene interpolymer in which the comonomer is randomly distributed within a given polymer molecule and wherein substantially all of the polymer molecules have the same ethylene to comonomer molar ratio. The term refers to an ethylene interpolymer that are manufactured using so-called homogeneous catalyst systems known in the art such Ziegler vanadium, hafnium and zirconium catalyst systems and metallocene catalyst systems (e.g., a constrained geometry catalyst systems) as described by Elston in U.S. Pat. No. 3,645,992; Stevens et al. in U.S. Pat. No. 5,064,802 and EP 0 416 815 A2; Canich in U.S. Pat. No. 5,026,798 and U.S. Pat. No. 5,055,438; Parikh et al. in WO 93/13143; and Kolthammer et al. in WO 94/17112, the disclosures of all of which are incorporated herein by reference.

Homogeneously branched ethylene polymers for use in the present invention can be also described as having less than 15 weight percent, preferably less 10 weight percent, more preferably less than 5 and most preferably zero (0) weight percent of the polymer with a degree of short chain branching less than or equal to 10 methyls/1000 carbons. That is, the polymer contains no measurable high density polymer fraction (e.g., there is no fraction having a density of equal to or greater than 0.94 g/cm$^3$), as determined, for example, using a temperature rising elution fractionation (TREF) technique and infrared or 13C nuclear magnetic resonance (NMR) analysis.

Preferably, the homogeneously branched ethylene polymer is characterized as having a narrow, essentially single melting TREF profile/curve and essentially lacking a measurable high density polymer portion, as determined using a temperature rising elution fractionation technique (abbreviated herein as "TREF").

The composition distribution of an ethylene interpolymer can be readily determined from TREF as described, for example, by Wild et al., *Journal of Polymer Science, Poly. Phys. Ed.*, Vol. 20, p. 441 (1982), or in U.S. Pat. No. 4,798,081; U.S. Pat. No. 5,008,204; or by L. D. Cady, "The Role of Comonomer Type and Distribution in LLDPE Product Performance," SPE Regional Technical Conference, Quaker Square Hilton, Akron, Ohio, October 1–2, pp. 107–119 (1985), the disclosures of all which are incorporated herein by reference.

The composition (monomer) distribution of the interpolymer can also be determined using $^{13}C$ NMR analysis in accordance with techniques described in U.S. Pat. No. 5,292,845; U.S. Pat. No. 4,798,081; U.S. Pat. No. 5,089,321 and by J. C. Randall, *Rev. Macromol. Chem. Phys.*, C29, pp. 201–317, the disclosures of all of which are incorporated herein by reference.

In analytical temperature rising elution fractionation analysis (as described in U.S. Pat. No. 4,798,081 and abbreviated herein as "ATREF"), the film or composition to be analyzed is dissolved in a suitable hot solvent (e.g., trichlorobenzene) and allowed to crystallized in a column containing an inert support (stainless steel shot) by slowly reducing the temperature. The column is equipped with both a refractive index detector and a differential viscometer (DV) detector. An ATREF-DV chromatogram curve is then generated by eluting the crystallized polymer sample from the column by slowly increasing the temperature of the eluting solvent (trichlorobenzene). The ATREF curve is also frequently called the short chain branching distribution (SCBD) or composition distribution (CD) curve, since it indicates how evenly the comonomer (e.g., octene) is distributed throughout the sample in that as elution temperature decreases, comonomer content increases. The refractive index detector provides the short chain distribution information and the differential viscometer detector provides an estimate of the viscosity average molecular weight. The composition distribution and other compositional information can also be determined using crystallization analysis fractionation such as the CRYSTAF fractionalysis package available commercially from PolymerChar, Valencia, Spain.

Preferred homogeneously branched ethylene polymers (such as, but not limited to, substantially linear ethylene polymers) have a single melting peak between −30 and 150° C., as determined using differential scanning calorimetry (DSC), as opposed to traditional Ziegler polymerized heterogeneously branched ethylene polymers (e.g., LLDPE and ULDPE or VLDPE) which have two or more melting points.

The single melting peak is determined using a differential scanning calorimeter standardized with indium and deionized water. The method involves about 5–7 mg sample sizes, a "first heat" to about 180° C. which is held for 4 minutes, a cool down at 10° C./min. to −30° C. which is held for 3 minutes, and heat up at 10° C./min. to 150° C. to provide a "second heat" heat flow vs. temperature curve from which the melt peak(s) is taken. Total heat of fusion of the polymer is calculated from the area under the curve.

The homogeneously branched ethylene polymers for use in the invention can be either a substantially linear ethylene polymer or a homogeneously branched linear ethylene polymer.

The term "linear" as used herein means that the ethylene polymer does not have long chain branching. That is, the polymer chains comprising the bulk linear ethylene polymer have an absence of long chain branching, as in the case of traditional linear low density polyethylene polymers or linear high density polyethylene polymers made using Ziegler polymerization processes (e.g., U.S. Pat. No. 4,076,698 (Anderson et al.)), sometimes called heterogeneous polymers. The term "linear" does not refer to bulk high pressure branched polyethylene, ethylene/vinyl acetate copolymers, or ethylene/vinyl alcohol copolymers which are known to those skilled in the art to have numerous long chain branches.

The term "homogeneously branched linear ethylene polymer" refers to polymers having a narrow short chain branching distribution and an absence of long chain branching. Such "linear" uniformly branched or homogeneous polymers include those made as described in U.S. Pat. No. 3,645,992 (Elston) and those made using so-called single site catalysts in a batch reactor having relatively high ethylene concentrations (as described in U.S. Pat. No. 5,026,798 (Canich) or in U.S. Pat. No. 5,055,438 (Canich)) or those made using constrained geometry catalysts in a batch reactor also having relatively high olefin concentrations (as described in U.S. Pat. No. 5,064,802 (Stevens et al.) or in European Patent No. 0 416 815 A2 (Stevens et al.)).

Typically, homogeneously branched linear ethylene polymers are ethylene/α-olefin interpolymers, wherein the α-olefin is at least one $C_3$–$C_{20}$ α-olefin (e.g., propylene, 1-butene, 1-pentene, 4-methyl-1-pentene, 1-hexene, 1-heptene, and 1-octene) and preferably the at least one $C_3$–$C_{20}$ α-olefin is 1-butene, 1-hexene, 1-heptene or 1-octene. Most preferably, the ethylene/α-olefin interpolymer is a copolymer of ethylene and a $C_3$–$C_{20}$ α-olefin, and especially an ethylene/$C_4$–$C_8$ α-olefin copolymer such as an ethylene/1-octene copolymer, ethylene/1-butene copolymer, ethylene/1-pentene copolymer or ethylene/1-hexene copolymer.

Suitable homogeneously branched linear ethylene polymers for use in the invention are sold under the designation of TAFMER by Mitsui Chemical Corporation and under the designations of EXACT and EXCEED resins by Exxon Chemical Company.

The term "substantially linear ethylene polymer" as used herein means that the bulk ethylene polymer is substituted, on average, with about 0.01 long chain branches/1000 total carbons to about 3 long chain branches/1000 total carbons (wherein "total carbons" includes both backbone and branch carbons). Preferred polymers are substituted with about 0.01 long chain branches/1000 total carbons to about 1 long chain branches/1000 total carbons, more preferably from about 0.05 long chain branches/1000 total carbons to about 1 long chain branched/1000 total carbons, and especially from about 0.3 long chain branches/1000 total carbons to about 1 long chain branches/1000 total carbons.

As used herein, the term "backbone" refers to a discrete molecule, and the term "polymer" or "bulk polymer" refers, in the conventional sense, to the polymer as formed in a reactor. For the polymer to be a "substantially linear ethylene polymer", the polymer must have at least enough molecules with long chain branching such that the average long chain branching in the bulk polymer is at least an average of from about 0.01/1000 total carbons to about 3 long chain branches/1000 total carbons.

The term "bulk polymer" as used herein means the polymer which results from the polymerization process as a mixture of polymer molecules and, for substantially linear ethylene polymers, includes molecules having an absence of long chain branching as well as molecules having long chain branching. Thus a "bulk polymer" includes all molecules formed during polymerization. It is understood that, for the substantially linear polymers, not all molecules have long chain branching, but a sufficient amount do such that the average long chain branching content of the bulk polymer positively affects the melt rheology (i.e., the shear viscosity and melt fracture properties) as described herein below and elsewhere in the literature.

Long chain branching (LCB) is defined herein as a chain length of at least one (1) carbon less than the number of carbons in the comonomer, whereas short chain branching (SCB) is defined herein as a chain length of the same number of carbons in the residue of the comonomer after it is incorporated into the polymer 2 5 molecule backbone. For example, a substantially linear ethylene/1-octene polymer has backbones with long chain branches of at least seven (7) carbons in length, but it also has short chain branches of only six (6) carbons in length.

Long chain branching can be distinguished from short chain branching by using $^{13}C$ nuclear magnetic resonance (NMR) spectroscopy and to a limited extent, e.g. for ethylene homopolymers, it can be quantified using the method of Randall, (*Rev. Macromol.Chem. Phys.*, C29 (2&3), p. 285–297), the disclosure of which is incorporated herein by reference. However as a practical matter, current $^{13}$C nuclear magnetic resonance spectroscopy cannot determine the length of a long chain branch in excess of about six (6) carbon atoms and as such, this analytical technique cannot distinguish between a seven (7) carbon branch and a seventy (70) carbon branch. The long chain branch can be as long as about the same length as the length of the polymer backbone.

Although conventional $^{13}$C nuclear magnetic resonance spectroscopy cannot determine the length of a long chain branch in excess of six carbon atoms, there are other known techniques useful for quantifying or determining the presence of long chain branches in ethylene polymers, including ethylene/1-octene interpolymers. For example, U.S. Pat. No. 4,500,648, incorporated herein by reference, teaches that long chain branching frequency (LCB) can be represented by the equation LCB=b/$M_w$, wherein b is the weight average number of long chain branches per molecule and $M_w$ is the weight average molecular weight. The molecular weight averages and the long chain branching characteristics are determined by gel permeation chromatography and intrinsic viscosity methods, respectively.

Two other useful methods for quantifying or determining the presence of long chain branches in ethylene polymers, including ethylene/1-octene interpolymers are gel permeation chromatography coupled with a low angle laser light scattering detector (GPC-LALLS) and gel permeation chromatography coupled with a differential viscometer detector (GPC-DV). The use of these techniques for long chain branch detection and the underlying theories have been well documented in the literature. See, e.g., Zimm, G. H. and Stockmayer, W. H., *J. Chem. Phys.*, 17,1301 (1949) and Rudin, A., *Modern Methods of Polymer Characterization*, John Wiley & Sons, New York (1991) pp. 103–112, the disclosures of both of which are incorporated by reference.

A. Willem deGroot and P. Steve Chum, both of The Dow Chemical Company, at the Oct. 4, 1994 conference of the Federation of Analytical Chemistry and Spectroscopy Society (FACSS) in St. Louis, Mo., presented data demonstrating that GPC-DV is indeed a useful technique for quantifying the presence of long chain branches in substantially linear ethylene polymers. In particular, deGroot and Chum found that the level of long chain branches in substantially linear ethylene homopolymer samples measured using the Zimm-Stockmayer equation correlated well with the level of long chain branches measured using $^{13}$C NMR.

Further, deGroot and Chum found that the presence of octene does not change the hydrodynamic volume of the polyethylene samples in solution and, as such, one can account for the molecular weight increase attributable to octene short chain branches by knowing the mole percent octene in the sample. By deconvoluting the contribution to molecular weight increase attributable to 1-octene short chain branches, deGroot and Chum showed that GPC-DV may be used to quantify the level of long chain branches in substantially linear ethylene/octene copolymers.

DeGroot and Chum also showed that a plot of Log($I_2$, melt index) as a function of Log(GPC Weight Average Molecular Weight) as determined by GPC-DV illustrates that the long chain branching aspects (but not the extent of long branching) of substantially linear ethylene polymers are comparable to that of high pressure, highly branched low density polyethylene (LDPE) and are clearly distinct from ethylene polymers produced using Ziegler-type catalysts such as titanium complexes and ordinary homogeneous catalysts such as hafnium and vanadium complexes.

For substantially linear ethylene polymers, the empirical effect of the presence of long chain branching is manifested as enhanced Theological properties which are quantified and expressed in terms of gas extrusion rheometry (GER) results and/or melt flow, $I_{10}/I_2$, increases.

The substantially linear ethylene polymers used in the present invention are a unique class of compounds that are further defined in U.S. Pat. No. 5,272,236, application Ser. No. 07/776,130, filed Oct. 15, 1991; U.S. Pat. No. 5,278,272, application Ser. No. 07/939,281, filed Sep. 2, 1992; and U.S. Pat. No. 5,665,800, application Ser. No. 08/730,766, filed Oct. 16, 1996, each of which is incorporated herein by reference.

Substantially linear ethylene polymers differ significantly from the class of polymers conventionally known as homogeneously branched linear ethylene polymers described above and, for example, by Elston in U.S. Pat. No. 3,645,992. As an important distinction, substantially linear ethylene polymers do not have a linear polymer backbone in the conventional sense of the term "linear" as is the case for homogeneously branched linear ethylene polymers.

Substantially linear ethylene polymers also differ significantly from the class of polymers known conventionally as heterogeneously branched traditional Ziegler polymerized linear ethylene interpolymers (for example, ultra lowdensity polyethylene, linear low density polyethylene or high density polyethylene made, for example, using the technique disclosed by Anderson et al. in U.S. Pat. No. 4,076,698, in that substantially linear ethylene interpolymers are homogeneously branched polymers. Further, substantially linear ethylene polymers also differ from the class of heterogeneously branched ethylene polymers in that substantially linear ethylene polymers are characterized as essentially lacking a measurable high density or crystalline polymer fraction as determined using a temperature rising elution fractionation technique.

The homogeneously branched substantially linear ethylene polymers for use in the present invention is characterized as having (a) melt flow ratio, $I_{10}/I_2 \geq 5.63$, (b) a molecular weight distribution, $M_w/M_n$, as determined by gel permeation chromatography and defined by the equation:

$$(M_w/M_n) \leq (I_{10}/I_2) - 4.63,$$

(c) a gas extrusion rheology such that the critical shear rate at onset of surface melt fracture for the substantially linear ethylene polymer is at least 50 percent greater than the critical shear rate at the onset of surface melt fracture for a linear ethylene polymer, wherein the substantially linear ethylene polymer and the linear ethylene polymer comprise the same comonomer or comonomers, the linear ethylene polymer has an $I_2$ and $M_w/M_n$ within ten percent of the substantially linear ethylene polymer and wherein the respective critical shear rates of the substantially linear ethylene polymer and the linear ethylene polymer are measured at the same melt temperature using a gas extrusion rheometer, (d) a single differential scanning calorimetry, DSC, melting peak between −30° and 150° C., and (e) a density less than or equal to 0.865 g/cm$^3$.

Determination of the critical shear rate and critical shear stress in regards to melt fracture as well as other rheology properties such as "rheological processing index" (PI), is performed using a gas extrusion rheometer (GER). The gas extrusion rheometer is described by M. Shida, R. N. Shroff and L. V. Cancio in *Polymer Engineering Science*, Vol. 17, No. 11, p. 770 (1977) and in *Rheometers for Molten Plastics* by John Dealy, published by Van Nostrand Reinhold Co. (1982) on pp. 97–99, the disclosures of both of which are incorporated herein by reference.

The processing index (PI) is measured at a temperature of 190° C., at nitrogen pressure of 2500 psig using a 0.0296 inch (752 micrometers) diameter (preferably a 0.0143 inch diameter die for high flow polymers, e.g. 50–100 $I_2$ melt index or greater), 20:1 L/D die having an entrance angle of 180°. The GER processing index is calculated in millipoise units from the following equation:

$$PI = 2.15 \times 10^6 \text{ dyne/cm}^2/(1000 \times \text{shear rate}),$$

where: $2.15 \times 10^6$ dyne/cm$^2$ is the shear stress at 2500 psi, and the shear rate is the shear rate at the wall as represented by the following equation:

$$32 \text{ Q'}/(60 \text{ sec/min})(0.745)(\text{Diameter} \times 2.54 \text{ cm/in})^3, \text{ where:}$$

Q' is the extrusion rate (gms/min), 0.745 is the melt density of polyethylene (gm/cm$^3$), and Diameter is the orifice diameter of the capillary (inches).

The PI is the apparent viscosity of a material measured at apparent shear stress of $2.15 \times 10^6$ dyne/cm$^2$.

For substantially linear ethylene polymers, the PI is less than or equal to 70 percent of that of a conventional linear ethylene polymer having an $I_2$, $M_w/M_n$ and density each within ten percent of the substantially linear ethylene polymer.

An apparent shear stress vs. apparent shear rate plot is used to identify the melt fracture phenomena over a range of nitrogen pressures from 5250 to 500 psig using the die or GER test apparatus previously described. According to Ramamurthy in *Journal of Rheology*, 30(2), 337–357,1986, above a certain critical flow rate, the observed extrudate irregularities may be broadly classified into two main types: surface melt fracture and gross melt fracture.

Surface melt fracture occurs under apparently steady flow conditions and ranges in detail from loss of specular gloss to the more severe form of "sharkskin". In this disclosure, the onset of surface melt fracture is characterized at the beginning of losing extrudate gloss at which the surface roughness of extrudate can only be detected by 40×magnification. The critical shear rate at onset of surface melt fracture for the substantially linear ethylene polymers is at least 50 percent greater than the critical shear rate at the onset of surface melt fracture of a linear ethylene polymer having about the same $I_2$ and $M_w/M_n$. Preferably, the critical shear stress at onset of surface melt fracture for the substantially linear ethylene polymers of the invention is greater than about $2.8 \times 10^6$ dyne/cm$^2$.

Gross melt fracture occurs at unsteady flow conditions and ranges in detail from regular (alternating rough and smooth, helical, etc.) to random distortions. For commercial acceptability, (e.g., in blown film products), surface defects should be minimal, if not absent. The critical shear rate at onset of surface melt fracture (OSMF) and critical shear stress at onset of gross melt fracture (OGMF) will be used herein based on the changes of surface roughness and configurations of the extrudates extruded by a GER. For the substantially linear ethylene polymers used in the invention, the critical shear stress at onset of gross melt fracture is preferably greater than $4 \times 10^6$ dyne/cm$^2$.

For the processing index determination and for the GER melt fracture determination, substantially linear ethylene polymers are tested without inorganic fillers and do not have more than 20 ppm aluminum catalyst residue. Preferably, however, for the processing index and melt fracture tests, substantially linear ethylene polymers do contain antioxidants such as phenols, hindered phenols, phosphites or phosphonites, preferably a combination of a phenol or hindered phenol and a phosphite or a phosphonite.

The molecular weight distributions of ethylene polymers are determined by gel permeation chromatography (GPC) on a Waters 150C high temperature chromatographic unit equipped with a differential refractometer and three columns of mixed porosity. The columns are supplied by Polymer Laboratories and are commonly packed with pore sizes of $10^3$, $10^4$, $10^5$ and $10^6$ Å. The solvent is 1,2,4-trichlorobenzene, from which about 0.3 percent by weight solutions of the samples are prepared for injection. The flow rate is about 1.0 milliliters/minute, unit operating temperature is about 140° C. and the injection size is about 100 microliters.

The molecular weight determination with respect to the polymer backbone is deduced by using narrow molecular weight distribution polystyrene standards (from Polymer Laboratories) in conjunction with their elution volumes. The equivalent polyethylene molecular weights are determined by using appropriate Mark-Houwink coefficients for polyethylene and polystyrene (as described by Williams and Ward in *Journal of Polymer Science*, Polymer Letters, Vol. 6, p. 621, 1968, the disclosure of which is incorporated herein by reference) to derive the following equation:

$$M_{polyethylene} = a*(M_{polystyrene})^b.$$

In this equation, a=0.4316 and b=1.0. Weight average molecular weight, $M_w$, is calculated in the usual manner according to the following formula: $Mj = (\Sigma w_i(M_i^j))^j$. Where $w_i$ is the weight fraction of the molecules with molecular weight $M_i$ eluting from the GPC column in fraction i and j=1 when calculating $M_w$ and j=−1 when calculating $M_n$.

For the at least one homogeneously branched ethylene polymer used in the present invention, the $M_w/M_n$ is preferably less than 3.5, more preferably less than 3.0, most preferably less than 2.5, and especially in the range of from about 1.5 to about 2.5 and most especially in the range from about 1.8 to about 2.3.

Substantially linear ethylene polymers are known to have excellent processability, despite having a relatively narrow molecular weight distribution (that is, the $M_w/M_n$ ratio is typically less than 3.5). Surprisingly, unlike homogeneously and heterogeneously branched linear ethylene polymers, the melt flow ratio ($I_{10}/I_2$) of substantially linear ethylene polymers can be varied essentially independently of the molecular weight distribution, $M_w/M_n$. Accordingly, especially when good extrusion processability is desired, the preferred ethylene polymer for use in the present invention is a homogeneously branched substantially linear ethylene interpolymer.

Suitable constrained geometry catalysts for use manufacturing substantially linear ethylene polymers include constrained geometry catalysts as disclosed in U.S. application Ser. No. 07/545,403, filed Jul. 3, 1990; U.S. application Ser. No. 07/758,654, filed Sep. 12, 1991; U.S. Pat. No. 5,132,380 (application Ser. No. 07/758,654); U.S. Pat. No. 5,064,802 (application Ser. No. 07/547,728); U.S. Pat. No. 5,470,993 (application Ser. No. 08/241,523); U.S. Pat. No. 5,453,410 (application Ser. No. 08/108,693); U.S. Pat. No. 5,374,696 (application Ser. No. 08/08,003); U.S. Pat. No. 5,532,394 (application Ser. No. 08/295,768); U.S. Pat. No. 5,494,874 (application Ser. No. 08/294,469); and U.S. Pat. No. 5,189, 192 (application Ser. No. 07/647,111), the teachings of all of which are incorporated herein by reference.

Suitable catalyst complexes may also be prepared according to the teachings of WO 93/08199, and the patents issuing therefrom, all of which are incorporated herein by reference. Further, the monocyclopentadienyl transition metal olefin polymerization catalysts taught in U.S. Pat. No. 5,026,798, which is incorporated herein by reference, are also believed to be suitable for use in preparing the polymers of the present invention, so long as the polymerization conditions substantially conform to those described in U.S. Pat. No. 5,272,236; U.S. Pat. No. 5,278,272 and U.S. Pat. No. 5,665,800, especially with strict attention to the requirement of continuous polymerization. Such polymerization methods are also described in PCT/US 92/08812 (filed Oct. 15, 1992).

The foregoing catalysts may be further described as comprising a metal coordination complex comprising a metal of groups 3–10 or the Lanthanide series of the Periodic Table of the Elements and a delocalize β-bonded moiety substituted with a constrain-inducing moiety, said complex having a constrained geometry about the metal atom such that the angle at the metal between the centroid of the delocalized, substituted pi-bonded moiety and the center of at least one remaining substituent is less than such angle in a similar complex containing a similar pi-bonded moiety lacking in such constrain-inducing substituent, and provided further that for such complexes comprising more than one delocalized, substituted pi-bonded moiety, only one thereof for each metal atom of the complex is a cyclic, delocalized, substituted pi-bonded moiety. The catalyst further comprises an activating cocatalyst.

Suitable cocatalysts for use herein include polymeric or oligomeric aluminoxanes, especially methyl aluminoxane, as well as inert, compatible, noncoordinating, ion forming compounds. So called modified methyl aluminoxane (MMAO) is also suitable for use as a cocatalyst. One technique for preparing such modified aluminoxane is disclosed in U.S. Pat. No. 5,041,584, the disclosure of which is incorporated herein by reference. Aluminoxanes can also be made as disclosed in U.S. Pat. No. 5,218,071; U.S. Pat. No. 5,086,024; U.S. Pat. No. 5,041,585; U.S. Pat. No. 5,041,583; U.S. Pat. No. 5,015,749; U.S. Pat. No. 4,960,878; and U.S. Pat. No. 4,544,762, the disclosures of all of which are incorporated herein by reference.

Aluminoxanes, including modified methyl aluminoxanes, when used in the polymerization, are preferably used such that the catalyst residue remaining in the (finished) polymer is preferably in the range of from about 0 to about 20 ppm aluminum, especially from about 0 to about 10 ppm aluminum, and more preferably from about 0 to about 5 ppm aluminum. In order to measure the bulk polymer properties (e.g. PI or melt fracture), aqueous HCl is used to extract the aluminoxane from the polymer. Preferred cocatalysts, however, are inert, noncoordinating, boron compounds such as those described in EP 520732, the disclosure of which is incorporated herein by reference.

Substantially linear ethylene are produced via a continuous (as opposed to a batch) controlled polymerization process using at least one reactor (e.g., as disclosed in WO 93/07187, WO 93/07188, and WO 93/07189, the disclosure of each of which is incorporated herein by reference), but can also be produced using multiple reactors (e.g., using a multiple reactor configuration as described in U.S. Pat. No. 3,914,342, the disclosure of which is incorporated herein by reference) at a polymerization temperature and pressure sufficient to produce the interpolymers having the desired properties. The multiple reactors can be operated in series or in parallel, with at least one constrained geometry catalyst employed in at least one of the reactors.

Substantially linear ethylene polymers can be prepared via the continuous solution, slurry, or gas phase polymerization in the presence of a constrained geometry catalyst, such as the method disclosed in European Patent No.416,815-A, the disclosure of which is incorporated herein by reference. The polymerization can generally be performed in any reactor system known in the art including, but not limited to, a tank reactor(s), a sphere reactor(s), a recycling loop reactor(s) or combinations thereof, any reactor or all reactors operated partially or completely adiabatically, nonadiabatically or a combination of both. Preferably, a continuous loop-reactor solution polymerization process is used to manufacture the substantially linear ethylene polymer used in the present invention.

In general, the continuous polymerization required to manufacture substantially linear ethylene polymers may be accomplished at conditions well known in the prior art for Ziegler-Natta or Kaminsky-Sinn type polymerization reactions, that is, temperatures from 0 to 250° C. and pressures from atmospheric to 1000 atmospheres (100 MPa). Suspension, solution, slurry, gas phase or other process conditions may be employed if desired.

A support may be employed in the polymerization, but preferably the catalysts are used in a homogeneous (i.e., soluble) manner. It will, of course, be appreciated that the active catalyst system forms in situ if the catalyst and the cocatalyst components thereof are added directly to the polymerization process and a suitable solvent or diluent, including condensed monomer, is used in said polymerization process. It is, however, preferred to form the active catalyst in a separate step in a suitable solvent prior to adding the same to the polymerization mixture.

The substantially linear ethylene polymers used in the present invention are interpolymers of ethylene with at least one $C_3$–$C_{20}$ α-olefin and/or $C_4$–$C_{18}$ diolefin. Copolymers of ethylene and an α-olefin of $C_3$–$C_{20}$ carbon atoms are especially preferred. The term "interpolymer" as discussed above is used herein to indicate a copolymer, a terpolymer, or any other multiple monomer polymer, where at least one other comonomer is polymerized with ethylene or propylene to make the interpolymer.

Suitable unsaturated comonomers useful for polymerizing with ethylene include, for example, ethylenically unsaturated monomers, conjugated or non-conjugated dienes, polyenes, etc. Examples of such comonomers include $C_3$–$C_{20}$ α-olefins such as propylene, isobutylene, 1-butene, 1-hexene, 1-pentene, 4-methyl-1-pentene, 1-heptene, 1-octene, 1-nonene, and 1-decene. Preferred comonomers include propylene, 1-butene, 1-pentene, 1-hexene, 4-methyl-1-pentene and 1-octene, and 1-octene is especially preferred. Other suitable monomers include styrene, halo- or alkyl-substituted styrenes, vinylbenzocyclobutane, 1,4-hexadiene, 1,7-octadiene, and naphthenics (e.g., cyclopentene, cyclohexene and cyclooctene).

The homogeneously branched ethylene interpolymer can be blended with other polymers. Suitable polymers for blending with the ethylene interpolymer are commercially available from a variety of suppliers and include, but are not limited, an ethylene polymer (e.g., low density polyethylene, ultra or very low density polyethylene, medium density polyethylene, linear low density polyethylene, high density polyethylene, homogeneously branched linear ethylene polymer, substantially linear ethylene polymer, polystyrene, ethylene styrene interpolymer, ethylene vinyl acetate interpolymer, ethylene acrylic acid interpolymer, ethylene ethyl acetate interpolymer, ethylene methacrylic acid interpolymer, and ethylene methacrylic acid ionomer), polycarbonate, polystyrene, polypropylene (e.g., homopolymer polypropylene, polypropylene copolymer, and random block polypropylene interpolymer), thermoplastic polyurethane, polyamide, polylactic acid interpolymer, thermoplastic block polymer (e.g. styrene butadiene copolymer, styrene butadiene styrene triblock copolymer, and styrene ethylene-butylene styrene triblock copolymer), polyether block copolymer (e.g., PEBAX), copolyester polymer, polyester/polyether block polymers (for example, HYTREL), ethylene carbon monoxide interpolymer (e.g., ethylene/carbon monoxide (ECO), copolymer, ethylene/acrylic acid/carbon monoxide (EAACO) terpolymer, ethylene/methacrylic acid/carbon monoxide (EMAACO) terpolymer, ethylene/vinyl acetate/carbon monoxide (EVACO) terpolymer and styrene/carbon monoxide (SCO)), polyethylene terephthalate (PET), chlorinated polyethylene and mixtures thereof.

In one preferred embodiment, the homogeneously branched ethylene interpolymer is blended with a polypropylene resin, preferably an isotactic polypropylene resin such as Montell Profax 6323 and Amoco 4018. However, generally suitable polypropylene polymers for use in the invention, including random block propylene-ethylene polymers, are available from a number of manufacturers, such as, for example, Montell Polyolefins, DSM, Amoco, Eastman, Fina and Exxon Chemical Company. At Exxon, suitable polypropylene polymers are supplied under the designations ESCORENE and ACHIEVE.

Suitable poly lactic acid (PLA) polymers for use in the invention are well known in the literature (e.g., see D. M. Bigg et al., "Effect of Copolymer Ratio on the Crystallinity and Properties of Polylactic Acid Copolymers", ANTEC '96, pp. 2028–2039; WO 90/01521; EP 0 515203A; and EP 0 748846A2, the disclosures of each of which are incorporated herein by reference). Suitable poly lactic acid polymers are supplied commercially by Cargill Dow under the designation EcoPLA.

Suitable thermoplastic polyurethane for use in the invention are commercially available from The Dow Chemical Company under the designation PELLATHANE.

Suitable polyolefin carbon monoxide interpolymers can be manufactured using well known high pressure free-radical polymerization methods. However, they may also be manufactured using traditional Ziegler-Natta catalysis and even with the use of so-called homogeneous catalyst systems such as those described and referenced herein above.

Suitable free-radical initiated high pressure carbonyl-containing ethylene polymers such as ethylene acrylic acid interpolymers can be manufactured by any technique known in the art including the methods taught by Thomson and Waples in U.S. Pat. No. 3,520,861 and by McKinney et al. in U.S. Pat. Nos. 4,988,781; 4,599,392; and 5,384,373, the disclosures of which are incorporated herein by reference.

Suitable ethylene vinyl acetate interpolymers for use in the invention are commercially available from various suppliers, including Exxon Chemical Company and Du Pont Chemical Company.

Suitable ethylene/alkyl acrylate interpolymers are commercially available from various suppliers. Suitable ethylene/acrylic acid interpolymers are commercially available from The Dow Chemical Company under the designation PRIMACOR. Suitable ethylene/methacrylic acid interpolymers are commercially available from Du Pont Chemical Company under the designation NUCREL.

Chlorinated polyethylene (CPE), especially chlorinated substantially linear ethylene polymers, can be prepared by chlorinating polyethylene in accordance with well known techniques. Preferably, chlorinated polyethylene comprises equal to or greater than 30 weight percent chlorine. Suitable chlorinated polyethylenes for use in the invention are commercially supplied by The Dow Chemical Company under the designation TYRIN.

Suitable nitrogen-containing stabilizers for use in the present invention include, but are not limited to, naphthylamines (e.g. N-phenyl naphthylamines such as Naugard PAN supplied by Uniroyal); diphenylamine and derivatives thereof which are also referred to as secondary aromatic amines (e.g. 4,4'-bis( , -dimethylbenzyl)-diphenylamine which is supplied by Uniroyal Chemical under the designation Naugard® 445); p-phenylenediamines (e.g. Wingstay® 300 supplied by Goodyear); piperidines and derivatives thereof (e.g., polymeric N,N'-bis(2,2,6,6-tetramethyl-4-piperidinyl)-1,6-hexanediamine with 2,4,6-trichloro-1,3,5-triazine and 2,4,4-trimethyl-1,2-pentanamine which is supplied by Ciba-Geigy under the designation of Chimassorb® 944 as well as other substituted piperidines such as Chimassorb® 119, Tinuvin® 622 and Tinuvin® 770, all three also supplied by Ciba-Geigy), and quinolines (e.g. oxyquinolines and hydroquinolines such as polymeric 2,2,4-trimethyl-1,2-dihydroquinoline which is supplied by Vanderbilt Company under the designation s Agerite® D).

Suitable nitrogenontaining stabilizers also include the hybrid stabilizers such as aminophenols (e.g. N,N'-hexamethylenebis-3-(3,5-di-tert-butyl-4-hydroxyphenyl)-propionamide), acylaminophenols (which are also referred to as 4-hydroyanilides) and the various hybrid stabilizers described in U.S. Pat. No. 5,122,593(the disclosure of which is incorporated herein by reference) which consist of a N-(substituted)-1-(piperazine-2-one alkyl) group at one end and a (3,5-dialkyl-4-hydroxyphenyl)-α,α-disubstituted acetamine at the other end.

Other suitable nitrogen-containing stabilizers include carboxylic acid amides of aromatic mono and dicarboxylic acids and N-monosubstituted derivatives (e.g N,N'-diphenyloxamide and 2,2'-oxamidobisethyl 3-(3,5-di-tert-butyl-4-hydroxyphenyl) propionate which is supplied by Uniroyal Chemical under the designation Naugard® XL-1); hydrazides of aliphatic and aromatic mono- and dicarboxylic acids and N-acylated derivatives thereof; bis-acylated hydrazine derivatives; melamine; benzotriazoles, hydrazones; acylated derivatives of hydrazino-triazines; polyhydrazides; salicylaethylenediimines; salicylaloximes; derivatives of ethylenediamino tetraacetic acid; and aminotriazoles and acylated derivatives thereof.

Preferred nitrogen-containing stabilizers for use in the present invention are diphenylamines, substituted piperidines and hydroquinolines. Further, the at least one nitrogen-containing stabilizer can be employed alone or in combination with another stabilizer and antioxidant such as, for example, but not limited to, other nitrogen-containing stabilizer as well as a hindered phenol (e.g., 2,6-di-tert-butyl-4-methylphenol which is supplied by Koppers Chemical under the designation BHT® and tetrakis(methylene 3-(3,5-di-tert-butyl-4-hydroxyphenyl) propionate) methane which is supplied by Ciba-Geigy under the designation Irganox® 1010); thioester (e.g. dilauryl thiodipropionate which is supplied by Evans under the designation Evanstab® 12); phosphite (e.g., Irgafos® 168 supplied by Ciba-Geigy Corp. and tri(nonylphenyl) phosphite which is supplied by Uniroyal Chemical under the designation Naugard® P); diphosphite (e.g. distearyl pentaerthritol diphosphite which is supplied by Borg-Warner under the designation Weston® 618); polymeric phosphite (e.g. Wytox® 345-S(1) supplied by Olin); phosphited phenol and bisphenol (e.g. Wytox® 604 supplied by Olin); and diphosphonite (e.g., tetrakis(2,4-di-tert-butylphenyl) 4,4'-biphenylylene diphosphonite which is supplied by Sandox under the designation Sandostab® P-EPQ).

The at least one nitrogen-containing stabilizer is add to the homogeneously branched ethylene polymer in a melt compounding step, preferably by the use of an additive concentrate, prior to fabrication and shaping process steps. The at least one nitrogen-containing stabilize can be added to the interpolymer at any effective concentration. However, preferably, the concentration of the least one nitrogen-containing stabilizer will for in the range of from about 0.05 to about 0.5 weight percent (based on the total weight of the stabilizer and interpolymer), more preferably in the range from about 0.075 to about 0.3 weight percent (based on the total weight of the stabilizer and the interpolymer) and most preferably in the range of from about 0.1 to about 0.25 weight percent (based on the total weight of the stabilizer and the interpolymer).

In-process additives, e.g. calcium stearate, water, and fluoropolymers, may also be used for purposes such as for the deactivation of residual catalyst or improved processability or both. Colorants, coupling agents and fire retardants may also be include as longer as their incorporation does not disturb the desirable characteristics of the inventive article, interpolymer or method.

The homogeneously branched ethylene interpolymer can also be filled or unfilled. If filled, then the amount of filler present should not exceed an amount that would adversely affect elevated temperature elasticity and/or the wash and dryability of the inventive article. Typically, the amount of filler present is between 20 and 80, preferably between 50 and 70, weight percent (wt percent) based on the total weight of the interpolymer. Representative fillers include kaolin clay, magnesium hydroxide, silica, calcium carbonate. In a preferred embodiment, in which a filler is present, the filler is coated with a material that will prevent or retard any tendency that the filler might otherwise have to interfere with desirable irradiation and/or crosslinking reactions and effects. Stearic acid is an illustrative example of such a protective filler coating, although other compound may be employed as protective filler coatings or treatments.

The improved elastic homogeneously branched ethylene interpolymer and elastic article of the invention have utility in a variety of applications. Suitable applications include, for example, but are not limited to, disposable personal hygiene products (e.g. training pants, diapers, absorbent underpants, incontinence products, and feminine.hygiene items); disposable and durable garments (e.g. elastic components in industrial apparel, coveralls, head coverings, underpants, pants, shirts, gloves, and socks); infection control/clean room products (e.g. surgical gowns and drapes, face masks, head coverings, surgical caps and hood, shoe coverings, boot slippers, wound dressings, bandages, sterilization wraps, wipers, lab coats, coverall, pants, aprons, jackets, and bedding items and sheets) and sports apparel.

Various homofil fibers can be made from the elastic ethylene interpolymer of the present invention, including staple fibers, spunbond fibers or melt blown fibers (using, e.g., systems as disclosed in U.S. Pat. No. 4,340,563 (Appel et al.), U.S. Pat. No. 4,663,220 (Wisneski et al.), U.S. Pat. No. 4,668,566 (Braun), or U.S. Pat. No. 4,322,027 (Reba), all of which are incorporated herein by reference), and gel spun fibers (e.g., the system disclosed in U.S. Pat. No. 4,413,110 (Kavesh et al.), incorporated herein by reference)). Staple fibers can be melt spun (i.e., they can be extruded into the final fiber diameter directly without additional drawing), or they can be melt spun into a higher diameter and subsequently hot or cold drawn to the desired diameter using conventional fiber drawing techniques.

Elastic staple fibers of the present invention herein can also be used as bonding fibers, especially where the inventive elastic fibers have a lower melting point than the surrounding matrix fibers. In a bonding fiber application, the bonding fiber is typically blended with other matrix fibers and the entire structure is subjected to heat, where the bonding fiber melts and bonds the surrounding matrix fiber. Typical matrix fibers which benefit from use of the inventive elastic fibers disclosed herein include, but are not limited to, poly(ethylene terephthalate) fibers, cotton fibers, nylon fibers, polypropylene fibers, heterogeneously branched polyethylene fibers, homogeneously branched ethylene polymer fibers, and linear polyethylene homopolymer fibers and combinations thereof. The diameter of the matrix fiber can vary depending upon the end use application.

Bicomponent fibers can also be made from the inventive elastic interpolymer described herein. Such bicomponent fibers have the elastic homogeneously branched ethylene interpolymer of the present invention in at least one portion of the fiber. For example, in a sheath/core bicomponent fiber (i.e., one in which the sheath concentrically surrounds the core), the stable, elastic homogeneously branched ethylene interpolymer can be in either the sheath or the core. Different elastic homogeneously branched ethylene interpolymers of the present invention can also be used independently as the sheath and the core in the same fiber, preferably where both components are elastic and especially where the sheath component has a lower melting point than the core component. Other types of bicomponent fibers are within the scope of the invention as well, and include such structures as side-by-side conjugated fibers (e.g., fibers having separate regions of polymers, wherein the elastic homogeneously branched ethylene interpolymer of the present invention comprises at least a portion of the fiber's surface).

The shape of the fiber is not limited. For example, typical fiber has a circular cross-sectional shape, but sometimes fibers have different shapes, such as a trilobal shape, or a flat (i.e., "ribbon" like) shape. The elastic fiber disclosed herein is not limited by the shape of the fiber.

Fiber diameter can be measured and reported in a variety of fashions. Generally, fiber diameter is measured in denier per filament. Denier is a textile term which is defined as the grams of the fiber per 9000 meters of that fiber's length. Monofilament generally refers to an extruded strand having a denier per filament greater than 15, usually greater than 30. Fine denier fiber generally refers to fiber having a denier of about 15 or less. Microdenier (aka microfiber) generally refers to fiber having a diameter not greater than about 100 micrometers. For the inventive elastic fibers disclosed herein, the diameter can be widely varied, with little impact upon the fiber's elasticity. However, the fiber denier can be adjusted to suit the capabilities of the finished article and as such, would preferably be: from about 0.5 to about 30 denier/filament for melt blown; from about 1 to about 30 denier/filament for spunbond; and from about 1 to about 20,000 denier/filament for continuous wound filament.

Fabrics made from the inventive stable, elastic fibers disclosed herein include both woven and nonwoven fabrics. Nonwoven fabrics can be made variously, including spunlaced (or hydrodynamically entangled) fabrics as disclosed in U.S. Pat. No. 3,485,706 (Evans) and U.S. Pat. No.

4,939,016 (Radwanski et al.), the disclosures of which are incorporated herein by reference; by carding and thermally bonding staple fibers; by spunbonding continuous fibers in one continuous operation; or by melt blowing fibers into fabric and subsequently calendering or thermally bonding the resultant web. These various nonwoven fabric manufacturing techniques are well known to those skilled in the art and the disclosure is not limited to any particular method. Other structures made from such fibers are also included within the scope of the invention, including e.g., blends of these novel stable, elastic fibers with other fibers (e.g., poly(ethylene terephthalate) (PET) or cotton).

Fabricated articles which can be made using the inventive stable, elastic fibersand fabrics disclosed herein include stable, elastic composite articles (e.g., diapers and undergarments) that have elastic portions. For example, elastic portions are typically constructed into diaper and undergarment waist band portions to prevent the diaper or undergarment from falling and into leg band portions to prevent leakage (as shown, for example, in U.S. Pat. No. 4,381,781 (Sciaraffa), the disclosure of which is incorporated herein by reference). Often, the elastic portions promote better form fitting and/or fastening systems for a good combination of comfort and reliability.

The inventive stable elastic fibers and fabrics disclosed herein can also produce structures which combine elasticity with breathability. For example, the inventive elastic fibers, fabrics and/or films of the present invention many be incorporated into the structures disclosed in U.S. provisional patent application No. 60/083,784, filed May 1, 1998 in name Maugans et al., the disclosure of which is incorporated herein by reference.

The inventive stable elastic fibers and fabrics disclosed herein can also be used in various structures as described in U.S. Pat. No. 2,957,512 (Wade), the disclosure of which is incorporated herein by reference. For example, layer 50 of the structure described in USP '512 (i.e., the elastic component) can be replaced with the inventive stable elastic fibers and fabrics, especially where flat, pleated, creped, crimped, etc., nonelastic materials are made into elastic structures. Attachment of the inventive stable elastic fibers and/or fabric disclosed herein to nonelastic fibers, fabrics or other structures can be done by melt bonding or with adhesives. Gathered or shirred elastic structures can be produced from the inventive stable elastic fibers and/or fabrics disclosed herein and nonelastic components by pleating the non-elastic component (as described in USP '512) prior to attachment, pre-stretching the elastic component prior to attachment, or heat shrinking the elastic component after attachment.

The inventive stable elastic fibers described herein also can be used in a spunlaced (or hydrodynamically entangled) process to make novel structures. For example, U.S. Pat. No. 4,801,482 (Goggans), the disclosure of which is incorporated herein by reference, discloses an elastic sheet (12) which can now be made with the novel elastic fibers/fabric described herein.

Continuous stable elastic filaments as described herein could also be used in woven applications where high resilience is desired.

The inventive stable elastic fibers and fabrics disclosed herein with adjust in the interpolymer melt index and/or degree of crosslinking or extent or radiation also have adjustable tenacity and retractive force. Such capabilities and characteristics enable extensive design flexibility, for example, to provide for variable retractive force in the same garment, if needed, as described for example in U.S. Pat. No. 5,196,000 (Clear et al.), the disclosure of which is incorporated herein by reference.

U.S. Pat. No. 5,037,416 (Allen et al.), the disclosure of which is incorporated herein by reference, describes the advantages of a form fitting top sheet by using elastic ribbons (see member 19 of USP '416). The inventive stable elastic fibers could serve the function of member 19 of USP '416, or could be used in fabric form to provide the desired elasticity.

Composites that utilize very high molecular weight linear polyethylene or copolymer polyethylene also benefit from the inventive stable elastic fibers disclosed herein. For example, the inventive elastic fibers have a low melting point (with the melting point of the polymer essentially linearly related to the polymer density), such that in a blend of inventive stable elastic fibers disclosed herein and very high molecular weight polyethylene fibers (e.g., Spectra™ fibers made by Allied Chemical) as described in U.S. Pat. No. 4,584,347 (Harpell et al.), the disclosure of which is incorporated herein by reference, the lower melting elastic fibers bond the high molecular weight polyethylene fibers without melting the high molecular weight fibers, thus preserving the high strength and integrity of the high molecular weight fiber.

In U.S. Pat. No. 4,981,747 (Morman), the inventive stable elastic fibers and/or fabrics disclosed herein can be substituted for elastic sheet 122, which forms a composite elastic material including a reversibly necked material.

The inventive stable elastic fibers disclosed herein can also be a melt blown elastic componlent, as described in reference 6 of the drawings of U.S. Pat. No. 4,879,170 (Radwanski), the disclosure of which is incorporated herein by reference. USP '170 generally describes elastic co-form material and manufacturing processes.

Elastic panels can also be made from the inventive stable elastic fibers and fabrics disclosed herein, and can be used, for example, as members 18, 20, 14, and/or 26 of U.S. Pat. No. 4,940,464 (Van Gompel), the disclosure of which is incorporated herein by reference. The inventive stable elastic fibers and fabrics described herein can also be used as elastic components of composite side panels (e.g., layer 86 of USP '464).

The stable elastic homogeneously branched ethylene interpolymer can also be shaped or fabricated into stable elastic films, coatings, sheets, strips, straps, and tapes, ribbons. The elastic film, coating and sheet of the present invention may be fabricated by any method known in the art, including blown bubble processes (e.g., simple bubble as well as biaxial orientation techniques such trapped bubble, double bubble and tenter framing), cast extrusion, injection molding processes, thermoforming processes, extrusion coating processes, profile extrusion, and sheet extrusion processes. Simple blown bubble film processes are described, for example, in *The Encyclopedia of Chemical Technology*, Kirk-Othmer, Third Edition, John Wiley & Sons, New York, 1981, Vol. 16, pp. 416–417 and Vol. 18, pp. 191–192. The cast extrusion method is described, for example, in Modem Plastics Mid-October 1989 Encyclopedia Issue, Volume 66, Number 11, pages 256 to 257. Injection molding, thermoforming, extrusion coating, profile extrusion, and sheet extrusion processes are described, for example, in Plastics Materials and Processes, Seymour S. Schwartz and Sidney H. Goodman, Van Nostrand Reinhold Company, New York, 1982, pp. 527–563, pp. 632–647, and pp. 596–602.

The stable elastic strips, tapes and ribbons of the present invention can be prepared by any known method, including the direct extrusion processing or by post-extrusion slitting, cutting or stamping techniques. Profile extrusion is an example of a primary extrusion process that is particularly suited to the preparation of tapes, strips and bands, ribbons.

The stable elastic materials of the present invention can also be rendered pervious or "breathable" by any method well known in the art including by apperturing, slitting, microperforating, mixing with fibers or foams and combinations thereof. Examples of such methods include, U.S. Pat. No. 3,156,242 by Crowe, Jr., U.S. Pat. No. 3,881,489 by Hartwell, U.S. Pat. No. 3,989,867 by Sisson and U.S. Pat. No. 5,085,654 by Buell, the disclosures of all of which are incorporate herein by reference.

Fabricated articles which can be made using the inventive stable elastic articles disclosed herein include composite fabric articles (e.g., disposable incontinence garments and diapers) that are comprised of one or more elastic component or portion. The inventive stable elastic articles disclosed herein can also produce fabric composite structures which combine elasticity with breathability by utilizing a technique that renders the elastic material pervious or "breathable" such as suggested by Lippert et al. in U.S. Pat. No. 4,861,652 and indicated above.

The inventive stable elastic articles disclosed herein can also be used in various structures as described in U.S. Pat. No. 2,957,512 (Wade), the disclosure of which is incorporated herein by reference. For example, layer 50 of the structure described in USP '512 (i.e., the elastic component) can be replaced with the novel stable elastic materials, especially where flat, pleated, and creped nonelastic materials are made into elastic or semi-elastic structures. Attachment of the novel stable elastic materials to nonelastic or less-elastic materials can be done with heat bonding or with adhesives. Gathered or shirred elastic composite materials can be produced from the new stable elastic material described herein and nonelastic components by pleating the non-elastic component (as described in USP '512) prior to attachment, prestretching the elastic component prior to attachment, or heat shrinking the elastic component after attachment.

The recovery after heat shrinking can be further enhanced by effectuating a high degree of orientation into the inventive stable elastic articles during fabrication. Significant orientation can be accomplished by the utilization of various known techniques such as high blow-up blown film fabrication, tenter framing of cast films and "double bubble" or "trapped bubble" blown film fabrication.

The inventive stable elastic articles described herein can also be used to make other novel structures. For example, U.S. Pat. No. 4,801,482 (Goggans), the disclosure of which is incorporated herein by reference, discloses an elastic sheet (12) which can now be made with the inventive stable elastic articles described herein.

The inventive stable elastic articles described herein can also be used to make breathable portion or breathable elastic composite materials. For example, U.S. Pat. No. 5,085,654 (Buell) discloses a leg band (15) with a breathable portion 45, a breathable topsheet (26), a breathable backsheet (25), elastic elements (31 and 64), a breathable element (54), and a breathable subelement (96) all or any combination of which can now be made with the inventive stable elastic articles disclosed herein in either pervious or impervious forms.

U.S. Pat. No. 5,037,416 (Allen et al.), the disclosure of which is incorporated herein by reference, describes the advantages of a form fitting top sheet by using elastic ribbons (member 12) and an elastic backsheet (member 16). Pervious stable inventive elastic articles described herein could serve the function of member 12 and impervious elastics materials of this invention could function as member 16, or disclosed elastic materials could be used in an elastic composite fabric form.

In U.S. Pat. No. 4,981,747 (Morman), the inventive stable elastic articles disclosed herein can be substituted for elastic sheets 12, 122 and 232 to construct an elastic composite material which includes a reversibly necked material.

Elastic panels, elements, or portions can also be made from the inventive stable elastic articles disclosed herein, and can be used, for example, as members 18, 20, 24, and/or 26 of U.S. Pat. No. 4,940,464 (Van Gompel), the disclosure of which is incorporated herein by reference. The inventive stable elastic articles described herein can also be used, for example, as elastic composite side panels (e.g., layer) or as elastic ribbons 42 and/or 44.

The following examples are provided to further illustrate and illuminate the present invention but is not intended to limit the invention to the specific embodiments set forth.

EXAMPLES

In an evaluation to determine the elastic performance of various ethylene polymers in response to irradiation or crosslinking, five different ethylene interpolymers were subjected to varying degrees of electron beam radiation and their elastic properties as 2 mil cast films were measured at room temperature. The polymer densities and the melt indexes of the ethylene polymers are shown in Table 1. All of the polymers were homogeneously branched ethylene/1-octene interpolymers supplied commercially by Dupont Dow Elastomers, Ltd., manufactured using a constrained geometry catalyst system and contained 2000 ppm Irganox 1010 thermal stabilizer. However, DDE 8190 also contained via blending 4–5 weight percent of isotactic polypropylene. The densities for the various polymers were determined in accordance with ASTM D-792 and the melt indexes were determined in accordance with ASTM D-1238 Condition 190° C./2.16 kilograms.

TABLE 1

| Polymer | Density (g/cm$^3$) | Melt Index (g/10 minutes) | Designation |
| --- | --- | --- | --- |
| A | 0.863 | 0.5 | ENGAGE EG 8180 |
| B | 0.859 | 1.0 | DDE 8190 |
| C | 0.870 | 1.0 | ENGAGE EG 8100 |
| D | 0.870 | 5.0 | ENGAGE EG 8200 |
| E | 0.870 | 10 | XU-58380.00 |

2 mil cast films of each polymer listed in Table 1 were fabricated using conventional cast film extrusion equipment at melt temperatures of 430°–500° F. After film fabrication, the cast films were electron beam radiated at various dosage using equipment similar to that described in U.S. Pat. No. 5,324,576, the disclosure of which is incorporated herein by reference. Except as otherwise indicated, the elastic properties (stress-strain data) for the various films were determined using an Instron tensiometer set at 10 inch/minute.

The percent permanent set and percent stress relaxation were determined for each sample at 23° C. For the permanent set determinations at 23° C., the gage length was 2 inches and the crosshead speed was 20 inches/minute. The test consisted of pulling the film sample to 200 percent strain (elongation) and holding it for 30 seconds, then taking the sample to 0 percent strain (elongation) and holding it at 0 percent strain for 60 seconds, and then pulling the sample to determine the point where the load initially rises above zero. The percent permanent set was taken as the percent strain at which the load rose above zero. The test was a one cycle test ran in duplicate.

For percent stress or load relaxation determinations at 23° C., the gage length was 2 inches and the crosshead speed was 20 inches/minute. These tests consisted of pulling film samples to 200 percent strain (elongation) and holding them there at 200 percent strain for 30 seconds. The stress initially at 200 percent strain was taken as the maximum stress and the stress after the 30 second holding period was taken as the minimum stress. The percent stress or load relaxation determinations were run in duplicate and was calculated from the following equation:

$$\frac{\text{maximum stress} - \text{minimum stress}}{\text{maximum stress}} \times 100.$$

Table 2 reports the elastic property (stress-strain) data as well as the permanent set and stress relaxation data for the various film samples.

Figure 2:
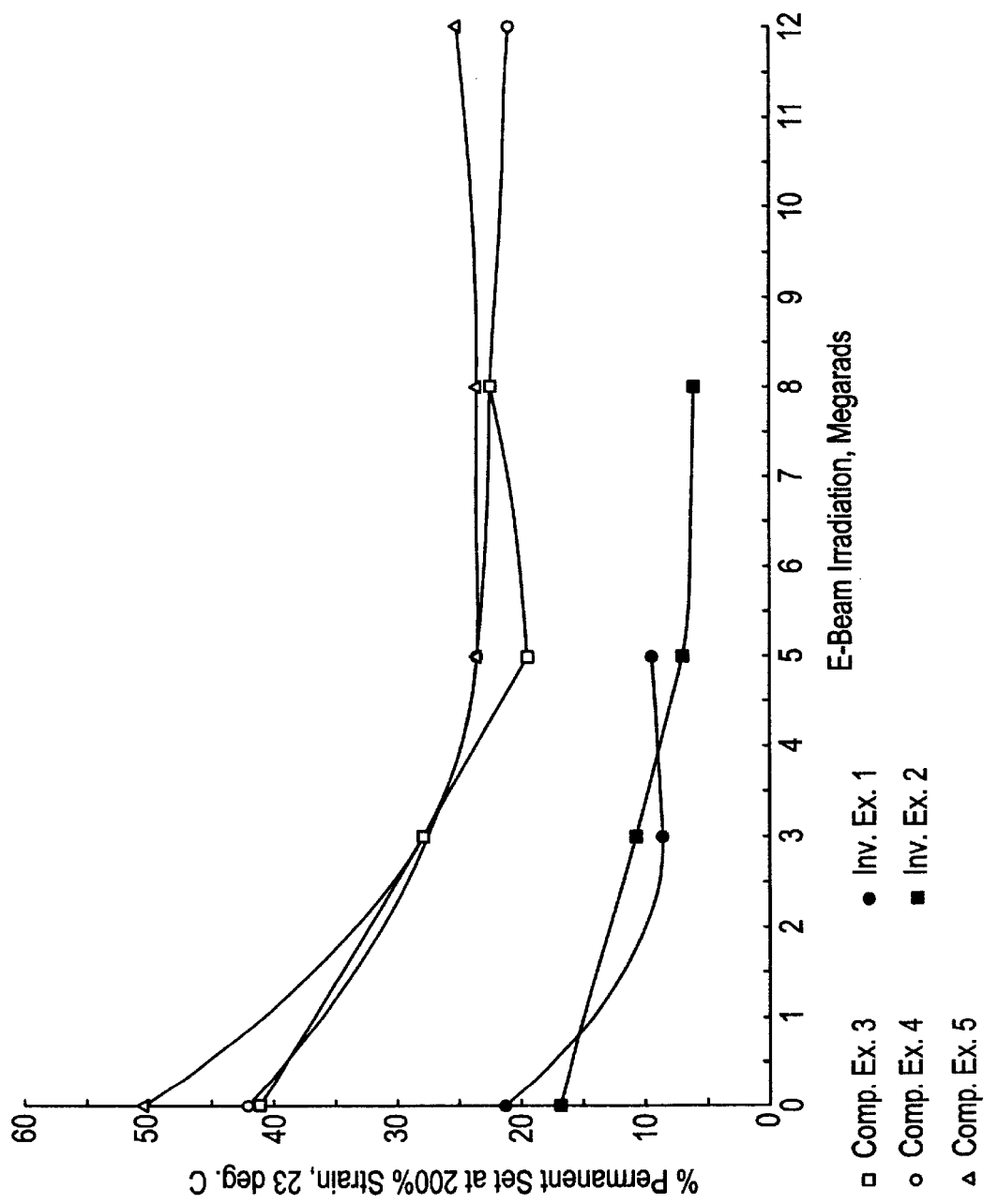
FIG. 2 is a plot of percent permanent set at 23° C. versus megarads of electron beam radiation for Inventive Examples 1 and 2 and comparative examples 3, 4 and 5.

Data in Table 2 were plotted and are shown in FIG. 1 and 2. FIG. 1 indicates that electron beam radiation up to 8–12 megarads has no substantial affect on the percent stress relaxation performance of the various polymers. Conversely, FIG. 2 shows that irradiation has a dramatic affect on the percent permanent set performance of the ethylene polymers. However, FIG. 2 (like FIG. 1 and the results shown in WO 95/29197) shows no particular distinction between the various polymers as polymer density dominated the percent permanent set response and radiation affected the various polymer equally.

Figure 3:
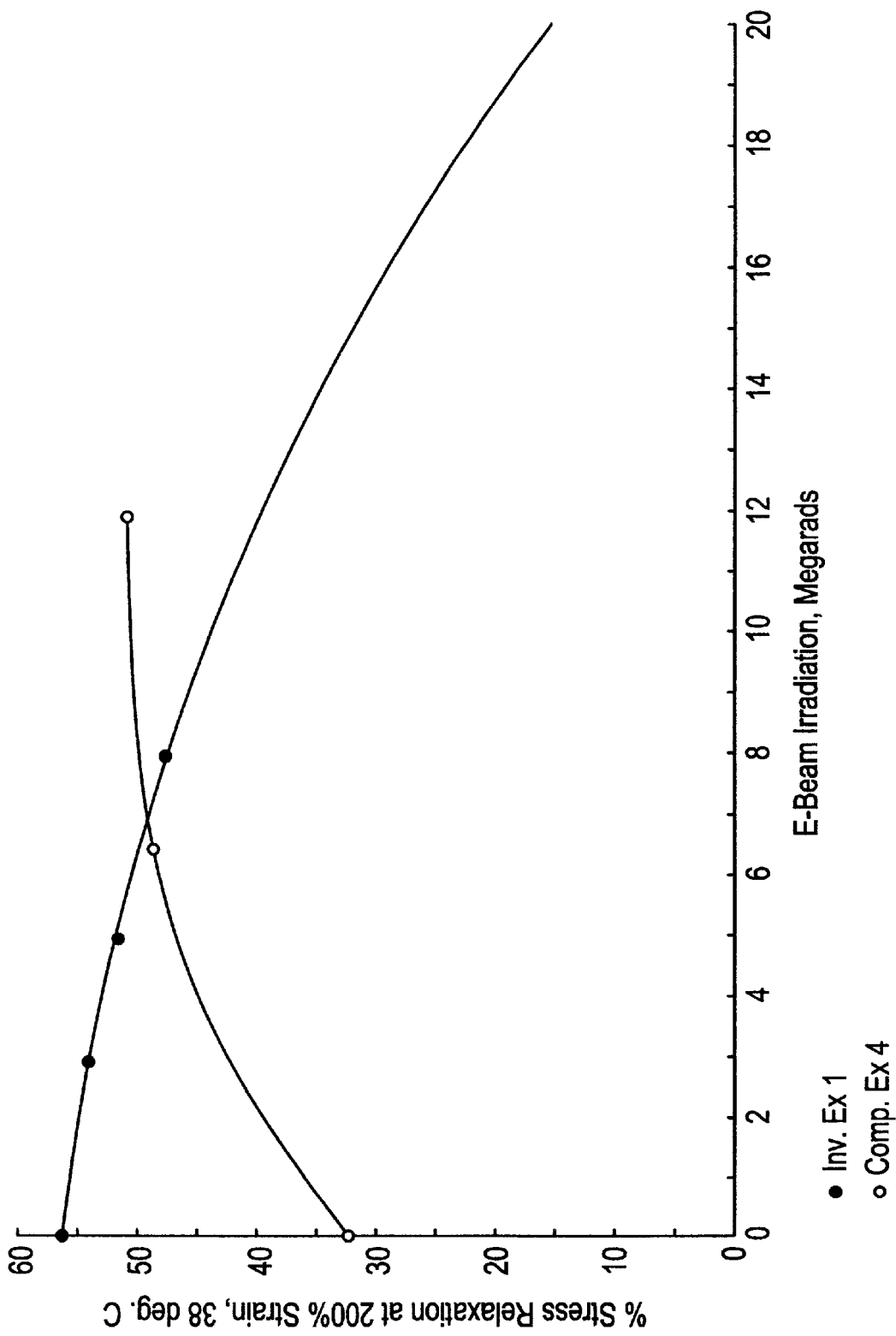
FIG. 3 is a plot of percent stress relaxation at 38° C. versus megarads of electron beam radiation for Inventive Example 1 and comparative example 4.

In another evaluation, 2 mil cast films of Resin A and Resin D were subjected to varying dosages of electron bean radiation and evaluated to determine their respective percent stress or load relaxation performances at 38° C. These tests were performed as described above, except the temperature was 38° C. instead of 23° C. and the samples were held at 200 percent strain for 1 hour instead for 30 seconds. Table 3 shows the results for this evaluation and FIG. 3 plots the results using the average of duplicative samples as well as a four-datapoint average for Resin D at 5 and 8 megarads of electron beam radiation.

TABLE 2

|  | * Inventive Ex. 1 | | | | * Inventive Ex. 2 | | | | Comparative Ex. 3* | | | |
|---|---|---|---|---|---|---|---|---|---|---|---|---|
| Resin | A | A | A | A | B | B | B | B | C | C | C | C |
| e-Beam, megarad | 0 | 3 | 5 | 8 | 0 | 3 | 5 | 8 | 0 | 3 | 5 | 8 |
| 100% Strain Load, g/inch | 232 | 242 | 254 | 259 | 191 | 170 | 211 | 214 | 330 | 315 | 318 | 327 |
| 200% Strain Load, g/inch | 269 | 290 | 318 | 354 | 226 | 211 | 235 | 238 | 409 | 384 | 380 | 395 |
| % Strain @ Break | 762 | 651 | 785 | 491 | 1109 | 896 | 973 | 860 | 667 | 676 | 697 | 410 |
| % Permanent Set @ 200% Strain | 21 | 9 | 10 | 22 | 17 | 11 | 7.5 | 6.6 | 41 | 28 | 20 | 23 |
| % Stress Relaxation @ 200% Strain | 19 | 18 | 16 | 19 | 20 | 17 | 19 | 20 | 22 | 20 | 25 | 21 |
| % Xylene Extractive | NA | 98.7 | 91.04 | 68.2 | NA | 99.6 | 99.1 | 99.6 | NA | 99.6 | 99.8 | 739 |

|  | Comparative Ex. 4* | | | | Comparative Ex. 5* | | | |
|---|---|---|---|---|---|---|---|---|
| Resin | D | D | D | D | E | E | E | E |
| e-Beam, megarad | 0 | 5 | 8 | 12 | 0 | 5 | 8 | 12 |
| 100% Strain Load, g/inch | 331 | 328 | 329 | 397 | 327 | 325 | 303 | 317 |
| 200% Strain Load, g/inch | 387 | 357 | 423 | 379 | 367 | 430 | 382 | 385 |
| % Strain @ Break | 812 | 780 | 883 | 784 | 909 | 869 | 809 | 773 |
| % Permanent Set @ 200% Strain | 42 | 24 | 35 | 22 | 50 | 24 | 24 | 26 |
| % Stress Relaxation @ 200% Strain | 23 | 18 | 23 | 19 | 23 | 23 | 22 | 21 |
| % Xylene Extractive | NA | 997 | 99.3 | 81.5 | NA | 99.6 | 99.4 | 77.5 |

*not an example of the invention; provided for comparamtially reduce (i.e., improve) the elevated temperature percent stress relaxation performance of ethylene interpolymers having densities less than 0.87 g/cm³ and conversely, show irradiation has no affect or increases the elevated temperature stress relaxation perforative purposes only.

TABLE 3

| E-Beam megarads | Maximum Stress, psi | Minimum Stress, psi | % Stress Relaxation |
|---|---|---|---|
| Resin D (Comp. Ex. 4) | | | |
| 0 | 192 | 127 | 33.9 |
| 0 | 181 | 125 | 30.9 |
| 5 | 235 | 112 | 52.3 |
| 5 | 230 | 108 | 53.0 |
| 8 | 231 | 132 | 42.9 |
| 8 | 245 | 136 | 44.5 |
| 12 | 250 | 120 | 52.0 |
| 12 | 227 | 115 | 49.3 |
| Resin A (Inv. Ex. 1) | | | |
| 0 | 126 | 55 | 56.3 |
| 0 | 120 | 53 | 55.8 |
| 3 | 120 | 57 | 52.5 |
| 3 | 134 | 59 | 56.0 |
| 5 | 134 | 64 | 52.2 |
| 5 | 142 | 69 | 51.4 |
| 8 | 137 | 70 | 48.9 |
| 8 | 145 | 78 | 46.2 |

The data in Table 3 and FIG. 3 show, surprisingly, that irradiation can substamtially reduce (i.e., improve) the elevated temperature percent stress relaxation performance of ethylene interpolymers having densities less than 0.87 g/cm³ and conversely, show irradiation has no affect or increases the elevated temperature stress relaxation performance of ethylene interpolymers characterized by higher densities. The data in Table 3 also show that the minimum stress of ethykene interpolymers characterized as having densities less than 0.87 g/cm$^3$ desirably increases at higher dosage level. Extrapolation of FIG. 3 indicates that at an electron beam radiation dosage level of about 20 megarads, such interpolymers will exhibit a percent stress relaxation at 38° C. of less than 20.

In another investigation, the effectiveness of various stabilizers was evaluated. In this investigation, 2 wt. percent stabilizer concentrates were prepared by first separately tumble dry blending a thioester stabilizer (i.e. Evanstab 12), a diphenylamine stabilizer (Naugard 445), a substituted piperidine stabilizer (i.e. Chimassorb 944) and a hydroquinoline stabilizer (i.e. Agerite D) with a homogeneously branched ethylene interpolymer (ENGAGE 8150 which had a target 0.78 g/cm$^3$ density and 0.5 g/10 minutes $I_2$ melt index). The dry blends were then melt extruded in a Berlyne extruder having a 20:1 L/D and equipped with a 1-inch diameter screw. The extrusion melt temperature was maintained at about 400° F., the various melts were pelletized and permitted to cool to ambient temperature.

Also, a 10 wt. percent concentrate of Irganox 1010 (a hindered phenolic stabilizer) was prepared using the same homogeneously branched ethylene interpolymer as above. However, the Irganox 1010 concentrate was prepared a Haake compounder set at a melt temperature of about 400° F. and a mixing residence.time of about 5 minutes. The Haake melt blend was removed from the mixing bowl after the 5 minute mixing residence time, permitted to cool to ambient temperature and then chopped into small granules.

The various stabilizer concentrates were tumble dry blended with two different homogeneously branched ethylene interpolymers, one nominally stabilized and the other non-stabilized, and both having a peak melting point less than 70° C. as determined using differential scanning calorimetry, to prepared various samples. The samples were then separately melt spun into fibers.

The fibers were separately melt spun on fiber extrusion equipment consisting of an extruder, gear pump and spinneret. The extruder was set to provide a melt temperature of about 236° C. Each polymer melt stream was feed to the gear pump which pressurized the melt and passed it through a 200 mesh pack followed by a 34-hole spinneret die. The spinneret had a 4:1 L/D and the holes had a diameter of about 800 microns. The resin output from the spinneret was controlled at about 0.78 grams/hole. The fibers were quenched with a room temperature air high-velocity blower and collected as free fall fiber samples. The resulting fibers an average diameter of about 800 microns. All stabilizers permitted the preparation of good quality fiber as there were no process upset or fiber surface defects associated with any stabilizer.

The various fiber samples were then irradiated using electron-beam radiation at 20 megarads. The irradiated fibers were then evaluated to determine their ability to resistance ordinary washing and long-term oven aging. To determine stability or resistance, a fiber sample was stretched to 200 percent strain (elongation) five times using an Instron tensiometer and then placed in a 160° F. wash solution. The wash solution consisted of 100 ppm of copper chloride and 0.5 weight percent Tide™ detergent regular household formula as supplied by Proctor and Gamble) and distilled water. The wash solution consisted of about 275 milliliters contained in a 500 ml wide-mouth beaker. The 160° F. wash temperature was maintained by the use of a hot plate equipped with a Variac and a thermo-watch device. Agitation of the wash solution was accomplished using a magnetic stirrer wherein the hot-plate provided the counter magnetic field currents to effectuate rotation of the magnetic stirrer. All fiber samples were placed in the wash solution at once (together) and were vigorously agitated for 30 minutes. After the 30 minute exposure to the wash solution, the fiber samples were carefully removed using tweezers and placed on paper towels to absorb excess wash solution. The washed fibers were then spaciously placed on Mylar™ film (polyester A type film available from The Pilcher Hamilton Company) and placed in a circulating air oven. The oven was set to 133° C. for 10 hours. After the 10-hour oven aging, the fiber samples were carefully (i.e. avoiding excessive handling and direct handling) removed from the oven and examined for visual indications of loss of integrity (e.g. melting and flowing or adhesion to the Mylar film or both). Table 4 sets forth the description of the various samples, provides descriptions of the samples following the wash and oven aging exposures and also provides a rank ordering of the resistance of the various samples to the wash/oven exposure. The results in Table 4 indicate that nitrogen-containing stabilizers such as Naugard 445, Chimassorb 944 and Agerite D are more effective than thioester or phenol stabilizer in stabilizing the elastic fibers against loss of integrity due to washing and oven aging. In particular, Table 4 shows that stabilizers such as Agerite D can provide outstanding protection such that there to is absolutely no melting of the fiber or adhesion to Mylar film.

Although the test described above can suitably and adequately distinguish the merits of the present invention, improved quantification can be conveniently accomplished by measuring fiber diameter (at the widest point) before the exposures and comparing those measurements to diameter measurements (at the widest point) taken after the exposures. Any measurable different in the diameters can be taken as a loss of integrity due to melting and flowing. However, a practitioner will recognize that indications of flowing-out or swelling are indicative of more substantial changes in integrity than melting and that adhesion to Mylar film generally reflects a less substantial change than melting.

Practitioners will also recognize that indication of melting must be made immediately when the sample is removed from the oven and that various aids can be used to help determine whether a polymer material is molten or not. Such aids may include, for example, a pin-point probe, a microscope, Polariod™ lenses, etc.

| | Resin | Additive (Target ppm) | Fiber Integrity Observations* | Rank Order |
|---|---|---|---|---|
| Comp. Ex. 6 | F | None | melting; adhesion when upside down | 8 |
| Comp. Ex. 7 | G | Evanstab 12 (1000) | melting; adhesion to 45–90° | 7 |
| Comp. Ex. 8 | G | None | flowing; melting; adhesion to 45–90° | 6 |
| Comp. Ex. 9 | G | Irganox 1010 (2000) | flowing; melting; adhesion to 30–45° | 5 |
| Comp. Ex. 10 | F | Irganox 1010 (2000) | adhesion to 45–90° | 4 |
| Inv. Ex. 11 | G | Naugard 445 (1000) | adhesion to <30° | 3 |
| Inv. Ex. 12 | G | Chimassorb 944 (1000) | adhesion to <30° | 2 |
| Inv. Ex. 13 | G | Agerite D (1000) | no adhesion; no melting; no flowing; no swelling | 1 |

Resin F is an ethylene-octene copolymer having a target density of 0.870 g/cm$^3$ and $I_2$ melt index of 5 g/10 minutes.

| Resin | Additive (Target ppm) | Fiber Integrity Observations* | Rank Order |
|---|---|---|---|

Resin G is an ethylene-octene copolymer having a target density of 0.870 g/cm³ and I₂ melt index of 0.5 g/10 minutes and containing 800 ppm Sandostab P-EPQ and 500 ppm Irganox 1076, Ciba-Geigy trademark for octadecyl 3-(3,5-di-tert-butyl-4-hydroxyphenyl) propionate which is a hindered phenol stabilizer.
*The degree notation as to adhesion refers to the angle that the Mylar film had to be deflected to unstick the given sample where 0° was the flat horizontal surface and 90° was approximately perpendicular to the flat horizontal surface, except Inv. Ex. 13 moved freely with the slightest handling of the film.

We claim:

1. A method of making a shaped and crosslinked article, the method of comprising the steps of:
   a. Shaping the article from a composition comprising (i) at least one homogeneously branched ethylene interpolymer that has a density of less than or equal to about 0.90 g/cc, and (ii) a nitrogen-containing stabilizer; and
   b. Crosslinking the article such that the article does not adhere to a polyester film upon deflection of the film from the article by more than 30 degrees, the adhesion of the article to the polyester film determined after the article has been washed for thirty minutes in an aqueous solution of 0.5 weight percent detergent, the solution maintained at 160° F., followed by ten hours of contact with the polyester film in a circulating air oven maintained at a temperature of 133° C., wherein the at least one homogeneously branched ethylene interpolymer is a substantially linear ethylene interpolymer characterized as having (a) melt flow ratio, $I_{10}/I_2 \geq 5.63$,
   (b) a molecular weight distribution, $M_w/M_n$, as determined by gel permeation chromatography and defined by the equation:

$$(M_w/M_n) \leq (I_{10}/I_2) - 4.63,$$

(c) a gas extrusion rheology such that the critical shear rate at onset of surface melt fracture for the substantially linear ethylene polymer is at least 50 percent greater than the critical shear rate at the onset of surface melt fracture for a linear ethylene polymer, wherein the substantially linear ethylene polymer and the linear ethylene polymer comprise the same comonomers or comonomers, the linear ethylene polymer has an $I_2$ and $M_w/M_n$ within ten percent of the substantially linear ethylene polymer and wherein the respective critical shear rates of the substantially linear ethylene polymer and the linear ethylene polymer are measured at the same melt temperature using a gas extrusion rheometer, and
   (d) a single differential scanning calorimetry, DSC, melting peak between −30° and 150° C., and wherein at least one nitrogen-containing stabilizer is selected from the group consisting of a hydroquinoline, diphenylamine and substituted piperidine.

2. The method of claim 1 in which the composition further comprises at least one pro-rad additive.

3. The method of claim 1 in which the ethylene interpolymer is grafted with a silane crosslinker.

4. The method of claim 3 in which the article is crosslinked upon exposure to ionizing radiation.

5. The method of claim 4, wherein the ionizing radiation is provided by electron beam irradiation.

6. The method of claim 1, wherein the article is fabricated using a technique selected from the group consisting of fiber melt spinning, fiber melt blowing, spunbonding, spunlacing, carding, film blowing, cast film, injection molding, pultrusion, thermoforming, stamping, forging, blow molding, sheet extrusion, solvent casting, solvent coating, thermal lamination, calendering, roll milling, reaction injection molding, extrusion coating, dispersion coating, and rotomolding.

7. The method of claim 1, wherein the homogeneously branched ethylene interpolymer is a homogeneously branched linear ethylene polymer.

8. The method of claim 7, wherein the homogeneously branched linear ethylene interpolymer is characterized as having a single differential scanning calorimetry, DSC, melting peak between −30° and 150° C.

9. The method of claim 1, wherein the homogeneously branched ethylene interpolymer is blended with another synthetic or natural polymer.

10. The method of claim 9, wherein the synthetic or natural polymer is an olefin polymer.

11. The method of claim 9, wherein the synthetic or natural polymer is a crystalline polyethylene having a density at 23° C. greater than or equal to 20 weight percent as determined using differential scanning calorimetry.

12. The method of claim 11, wherein the crystalline polyethylene has a density at 23° C. greater than or equal to 50 weight percent as determined using differential scanning calorimetry.

13. The method of claim 9, wherein the synthetic or natural polymer is a polypropylene.

14. The method of claim 13, wherein the polypropylene is an isotactic polypropylene polymer.

15. The method of claim 1, wherein the homogeneously branched ethylene interpolymer comprises ethylene interpolymerized with at least α-olefin.

16. The method of claim 15, wherein the α-olefin is a $C_3$–$C_{20}$ α-olefin.

17. The method of claim 1, wherein the homogeneously branched ethylene interpolymer comprises ethylene interpolymerized with propylene.

18. The method of claim 1 wherein the ethylene interpolymer comprises ethylene interpolymerized with a styrenic compound.

19. The method of claim 18, wherein the styrenic compound is styrene and the interpolymer is an ethylene-styrene interpolymer.

20. The method of claims 19, wherein the ethylene-styrene interpolymer comprises from about 0.5 to about 65 mole percent styrene, as determined using proton nuclear magnetic resonance analysis wherein
   (a) sample preparation is in 1,1,2,2-tetrachloroethane-$d_2$ (TCE-$d_2$) and
   (b) spectra are accumulated on a Varian VXR 300 unit with the sample probe at 80° C. and referenced to the residual protons of TCE-$d_2$ at 5.99 ppm.

21. The shaped interpolymer of claim 1 in the form of a woven or nonwoven fabric.

22. A personal hygiene item comprising the shaped interpolymer of claim 1.

23. The item of claim 22 wherein the item is a disposable diaper.

24. The item of claim 23 wherein the diaper comprises a backsheet or a topsheet comprised of the shaped interpolymer.

25. An infection control item comprising the shaped interpolymer of claim 1.

* * * * *